(12) United States Patent
Mountcastle et al.

(10) Patent No.: US 9,834,809 B2
(45) Date of Patent: Dec. 5, 2017

(54) SYRINGE FOR OBTAINING NANO-SIZED MATERIALS FOR SELECTIVE ASSAYS AND RELATED METHODS OF USE

(71) Applicant: LOCKHEED MARTIN CORPORATION, Bethesda, MD (US)

(72) Inventors: Paul D. Mountcastle, Moorestown, NJ (US); Svetlana M. Foulke, Liverpool, NY (US); John B. Stetson, Jr., New Hope, PA (US)

(73) Assignee: Lockheed Martin Corporation, Bethesda, MD (US)

( * ) Notice: Subject to any disclaimer, the term of this patent is extended or adjusted under 35 U.S.C. 154(b) by 7 days.

(21) Appl. No.: 14/193,007

(22) Filed: Feb. 28, 2014

(65) Prior Publication Data

US 2015/0247178 A1 Sep. 3, 2015

(51) Int. Cl.
*B01L 3/02* (2006.01)
*C12Q 1/24* (2006.01)
*A61B 5/15* (2006.01)
*A61B 5/153* (2006.01)

(52) U.S. Cl.
CPC ............ *C12Q 1/24* (2013.01); *A61B 5/15003* (2013.01); *A61B 5/153* (2013.01); *A61B 5/150732* (2013.01); *A61B 5/150755* (2013.01); *A61B 5/150236* (2013.01); *A61B 5/150244* (2013.01)

(58) Field of Classification Search
CPC .............. G01N 35/10; G01N 35/1002; G01N 35/1009; B01L 3/0217
USPC ................. 422/524, 525, 508, 509, 511, 515
See application file for complete search history.

(56) References Cited

U.S. PATENT DOCUMENTS

| 2,187,417 A | 1/1940 | Doble |
| 3,024,153 A | 3/1962 | Kennedy |
| 3,303,085 A | 2/1967 | Price et al. |
| 3,501,831 A | 3/1970 | Gordon |
| 3,593,854 A | 7/1971 | Swank .......................... 210/436 |
| 3,701,433 A | 10/1972 | Krakauer et al. ............. 210/436 |

(Continued)

FOREIGN PATENT DOCUMENTS

| CA | 2037988 | 9/1992 |
| CA | 2411935 | 12/2002 |

(Continued)

OTHER PUBLICATIONS

International Search Report and Written Opinion dated Jun. 3, 2015, corresponding to International Application No. PCT/US 2015/018114.

(Continued)

*Primary Examiner* — Jill Warden
*Assistant Examiner* — Brittany Fisher
(74) *Attorney, Agent, or Firm* — Foley & Lardner LLP

(57) ABSTRACT

A syringe for obtaining nano-sized components from a solution includes a barrel having an interior, a needle extending from one end of the barrel, and a plunger received in the interior at an end of the barrel opposite the needle. A filter cartridge is positioned between the needle and the barrel, wherein the filter cartridge maintains at least one membrane having apertures of two distinct size ranges, and wherein operation of the plunger to draw the solution into the barrel allows for retention of nano-sized components of a size between the two distinct size ranges.

10 Claims, 16 Drawing Sheets

(56) References Cited

U.S. PATENT DOCUMENTS

| | | | |
|---|---|---|---|
| 3,802,972 A | 4/1974 | Fleischer et al. | |
| 4,073,732 A | 2/1978 | Lauer et al. | 210/491 |
| 4,159,954 A | 7/1979 | Gangemi | 210/446 |
| 4,162,220 A | 7/1979 | Servas | 210/448 |
| 4,277,344 A | 7/1981 | Cadotte | |
| 4,303,530 A | 12/1981 | Shah et al. | 210/651 |
| 4,743,371 A | 5/1988 | Servas et al. | 210/188 |
| 4,855,058 A | 8/1989 | Holland et al. | |
| 4,880,440 A | 11/1989 | Perrin | |
| 4,889,626 A | 12/1989 | Browne | |
| 4,891,134 A | 1/1990 | Vcelka | |
| 4,925,560 A | 5/1990 | Sorrick | 210/387 |
| 4,935,207 A | 6/1990 | Stanbro et al. | |
| 4,976,858 A | 12/1990 | Kadoya | 210/496 |
| 5,052,444 A | 10/1991 | Messerly et al. | |
| 5,080,770 A | 1/1992 | Culkin | 204/182.3 |
| 5,156,628 A | 10/1992 | Kranz | |
| 5,182,111 A | 1/1993 | Aebischer et al. | |
| 5,185,086 A | 2/1993 | Kaali et al. | 210/748 |
| 5,201,767 A | 4/1993 | Caldarise et al. | |
| 5,244,981 A | 9/1993 | Seidner et al. | |
| 5,314,492 A | 5/1994 | Hamilton et al. | |
| 5,314,960 A | 5/1994 | Spinelli et al. | |
| 5,314,961 A | 5/1994 | Anton et al. | |
| 5,331,067 A | 7/1994 | Seidner et al. | |
| 5,344,454 A | 9/1994 | Clarke et al. | |
| 5,371,147 A | 12/1994 | Spinelli et al. | |
| 5,425,858 A | 6/1995 | Farmer | |
| 5,480,449 A | 1/1996 | Hamilton et al. | |
| 5,514,181 A | 5/1996 | Light et al. | |
| 5,516,522 A | 5/1996 | Peyman et al. | |
| 5,549,697 A | 8/1996 | Caldarise | |
| 5,562,944 A | 10/1996 | Kafrawy | |
| 5,565,210 A | 10/1996 | Rosenthal et al. | |
| 5,580,530 A | 12/1996 | Kowatsch et al. | |
| 5,595,621 A | 1/1997 | Light et al. | |
| 5,636,437 A | 6/1997 | Kaschmitter et al. | |
| 5,639,275 A | 6/1997 | Baetge et al. | |
| 5,641,323 A | 6/1997 | Caldarise | |
| 5,658,334 A | 8/1997 | Caldarise et al. | |
| 5,662,158 A | 9/1997 | Caldarise | |
| 5,665,118 A | 9/1997 | Lasalle et al. | |
| 5,671,897 A | 9/1997 | Ogg et al. | |
| 5,679,232 A | 10/1997 | Fedor et al. | |
| 5,679,249 A | 10/1997 | Fendya et al. | |
| 5,687,788 A | 11/1997 | Caldarise et al. | |
| 5,700,477 A | 12/1997 | Rosenthal et al. | |
| 5,713,410 A | 2/1998 | Lasalle et al. | |
| 5,716,412 A | 2/1998 | Decarlo et al. | |
| 5,716,414 A | 2/1998 | Caldarise | |
| 5,725,586 A | 3/1998 | Sommerich | |
| 5,731,360 A | 3/1998 | Pekala et al. | |
| 5,733,503 A | 3/1998 | Kowatsch et al. | |
| 5,746,272 A | 5/1998 | Mastrorio et al. | |
| 5,782,286 A | 7/1998 | Sommerich | |
| 5,782,289 A | 7/1998 | Mastrorio et al. | |
| 5,788,916 A | 8/1998 | Caldarise | |
| 5,800,828 A | 9/1998 | Dionne et al. | |
| 5,808,312 A | 9/1998 | Fukuda | |
| 5,868,727 A | 2/1999 | Barr et al. | |
| 5,897,592 A | 4/1999 | Caldarise et al. | |
| 5,902,762 A | 5/1999 | Mercuri et al. | |
| 5,906,234 A | 5/1999 | Mastrorio et al. | |
| 5,910,172 A | 6/1999 | Penenberg | |
| 5,910,173 A | 6/1999 | Decarlo et al. | |
| 5,913,998 A | 6/1999 | Butler et al. | |
| 5,925,247 A | 7/1999 | Huebbel | |
| 5,932,185 A | 8/1999 | Pekala et al. | |
| 5,935,084 A | 8/1999 | Southworth | |
| 5,935,172 A | 8/1999 | Ochoa et al. | |
| 5,954,937 A | 9/1999 | Farmer | |
| 5,974,973 A | 11/1999 | Tittgemeyer | |
| 5,976,555 A | 11/1999 | Liu et al. | |
| 5,980,718 A | 11/1999 | Van Konynenburg et al. | |
| 6,008,431 A | 12/1999 | Caldarise et al. | |
| 6,013,080 A | 1/2000 | Khalili | |
| 6,022,509 A | 2/2000 | Matthews et al. | |
| 6,052,608 A | 4/2000 | Young et al. | |
| 6,080,393 A | 6/2000 | Liu et al. | |
| 6,093,209 A | 7/2000 | Sanders | |
| 6,139,585 A | 10/2000 | Li | |
| 6,152,882 A | 11/2000 | Prutchi | |
| 6,156,323 A | 12/2000 | Verdicchio et al. | |
| 6,193,956 B1 | 2/2001 | Liu et al. | |
| 6,209,621 B1 | 4/2001 | Treacy | |
| 6,213,124 B1 | 4/2001 | Butterworth | |
| 6,228,123 B1 | 5/2001 | Dezzani | |
| 6,264,699 B1 | 7/2001 | Noiles et al. | |
| 6,292,704 B1 | 9/2001 | Malonek et al. | |
| 6,309,532 B1 | 10/2001 | Tran et al. | |
| 6,346,187 B1 | 2/2002 | Tran et al. | |
| 6,375,014 B1 | 4/2002 | Garcera et al. | |
| 6,426,214 B1 | 7/2002 | Butler et al. | |
| 6,454,095 B1 | 9/2002 | Brisebois et al. | |
| 6,455,115 B1 | 9/2002 | Demeyer | |
| 6,461,622 B2 | 10/2002 | Liu et al. | |
| 6,462,935 B1 | 10/2002 | Shiue et al. | |
| 6,521,865 B1 | 2/2003 | Jones et al. | |
| 6,532,386 B2 | 3/2003 | Sun et al. | |
| 6,580,598 B2 | 6/2003 | Shiue et al. | |
| 6,654,229 B2 | 11/2003 | Yanagisawa et al. | |
| 6,659,298 B2 | 12/2003 | Wong | |
| 6,660,150 B2 | 12/2003 | Conlan et al. | 204/627 |
| 6,661,643 B2 | 12/2003 | Shiue et al. | |
| 6,692,627 B1 | 2/2004 | Russell et al. | |
| 6,695,880 B1 | 2/2004 | Roffman et al. | |
| 6,699,684 B2 | 3/2004 | Ho et al. | |
| 6,719,740 B2 | 4/2004 | Burnett et al. | |
| 6,905,612 B2 * | 6/2005 | Dorian | B01D 15/02 210/219 |
| 6,924,190 B2 | 8/2005 | Dennison | |
| 7,014,829 B2 | 3/2006 | Yanagisawa et al. | |
| 7,071,406 B2 | 7/2006 | Smalley et al. | |
| 7,092,753 B2 | 8/2006 | Darvish et al. | |
| 7,138,042 B2 | 11/2006 | Tran et al. | |
| 7,171,263 B2 | 1/2007 | Darvish et al. | |
| 7,175,783 B2 | 2/2007 | Curran | |
| 7,179,419 B2 | 2/2007 | Lin et al. | |
| 7,190,997 B1 | 3/2007 | Darvish et al. | |
| 7,267,753 B2 | 9/2007 | Anex et al. | |
| 7,306,768 B2 | 12/2007 | Chiga | |
| 7,357,255 B2 | 4/2008 | Ginsberg et al. | |
| 7,374,677 B2 | 5/2008 | McLaughlin et al. | |
| 7,381,707 B2 | 6/2008 | Lin et al. | |
| 7,382,601 B2 | 6/2008 | Yoshimitsu | |
| 7,434,692 B2 | 10/2008 | Ginsberg et al. | |
| 7,452,547 B2 | 11/2008 | Lambino et al. | |
| 7,459,121 B2 | 12/2008 | Liang et al. | |
| 7,460,907 B1 | 12/2008 | Darvish et al. | |
| 7,476,222 B2 | 1/2009 | Sun et al. | |
| 7,477,939 B2 | 1/2009 | Sun et al. | |
| 7,477,940 B2 | 1/2009 | Sun et al. | |
| 7,477,941 B2 | 1/2009 | Sun et al. | |
| 7,479,133 B2 | 1/2009 | Sun et al. | |
| 7,505,250 B2 | 3/2009 | Cho et al. | |
| 7,531,094 B2 | 5/2009 | McLaughlin et al. | |
| 7,600,567 B2 | 10/2009 | Christopher et al. | |
| 7,631,764 B2 | 12/2009 | Ginsberg et al. | |
| 7,650,805 B2 | 1/2010 | Nauseda et al. | |
| 7,674,477 B1 | 3/2010 | Schmid et al. | |
| 7,706,128 B2 | 4/2010 | Bourcier | |
| 7,761,809 B2 | 7/2010 | Bukovec et al. | |
| 7,786,086 B2 | 8/2010 | Reches et al. | |
| 7,866,475 B2 | 1/2011 | Doskoczynski et al. | |
| 7,875,293 B2 | 1/2011 | Shults et al. | |
| 7,935,331 B2 | 5/2011 | Lin | |
| 7,935,416 B2 | 5/2011 | Yang et al. | |
| 7,943,167 B2 | 5/2011 | Kulkarni et al. | |
| 7,960,708 B2 | 6/2011 | Wolfe et al. | |
| 7,998,246 B2 | 8/2011 | Liu et al. | |
| 8,109,893 B2 | 2/2012 | Lande | |
| 8,147,599 B2 | 4/2012 | McAlister | |
| 8,262,943 B2 | 9/2012 | Meng et al. | |
| 8,308,702 B2 | 11/2012 | Batchvarova et al. | |

(56) References Cited

U.S. PATENT DOCUMENTS

| | | | |
|---|---|---|---|
| 8,316,865 B2 | 11/2012 | Ochs et al. | |
| 8,329,476 B2 * | 12/2012 | Pitkanen | C12M 33/04 422/513 |
| 8,354,296 B2 | 1/2013 | Dimitrakopoulos et al. | |
| 8,361,321 B2 | 1/2013 | Stetson et al. | 210/652 |
| 8,449,504 B2 | 5/2013 | Carter et al. | |
| 8,475,689 B2 | 7/2013 | Sun et al. | |
| 8,506,807 B2 | 8/2013 | Lee et al. | |
| 8,512,669 B2 | 8/2013 | Hauck | |
| 8,513,324 B2 | 8/2013 | Scales et al. | |
| 8,535,726 B2 | 9/2013 | Dai et al. | |
| 8,592,291 B2 | 11/2013 | Shi et al. | |
| 8,617,411 B2 | 12/2013 | Singh | |
| 8,666,471 B2 | 3/2014 | Rogers et al. | |
| 8,686,249 B1 | 4/2014 | Whitaker et al. | |
| 8,697,230 B2 | 4/2014 | Ago et al. | |
| 8,698,481 B2 | 4/2014 | Lieber et al. | |
| 8,715,329 B2 | 5/2014 | Robinson et al. | |
| 8,721,074 B2 | 5/2014 | Pugh et al. | |
| 8,734,421 B2 | 5/2014 | Sun et al. | |
| 8,744,567 B2 | 6/2014 | Fassih et al. | |
| 8,751,015 B2 | 6/2014 | Frewin et al. | |
| 8,753,468 B2 | 6/2014 | Caldwell et al. | |
| 8,759,153 B2 | 6/2014 | Elian et al. | |
| 8,808,257 B2 | 8/2014 | Pugh et al. | |
| 8,828,211 B2 | 9/2014 | Garaj et al. | |
| 8,840,552 B2 | 9/2014 | Brauker et al. | |
| 8,857,983 B2 | 10/2014 | Pugh et al. | |
| 8,861,821 B2 | 10/2014 | Osumi | |
| 8,894,201 B2 | 11/2014 | Pugh et al. | |
| 8,940,552 B2 | 1/2015 | Pugh et al. | |
| 8,950,862 B2 | 2/2015 | Pugh et al. | |
| 8,974,055 B2 | 3/2015 | Pugh et al. | |
| 8,975,121 B2 | 3/2015 | Pugh et al. | |
| 8,979,978 B2 | 3/2015 | Miller et al. | |
| 8,986,932 B2 | 3/2015 | Turner et al. | |
| 8,993,234 B2 | 3/2015 | Turner et al. | |
| 8,993,327 B2 | 3/2015 | McKnight et al. | |
| 9,014,639 B2 | 4/2015 | Pugh et al. | |
| 9,017,937 B1 | 4/2015 | Turner et al. | |
| 9,023,220 B2 | 5/2015 | Zurutuza Elorza et al. | |
| 9,028,663 B2 | 5/2015 | Stetson et al. | |
| 9,035,282 B2 | 5/2015 | Dimitrakopoulos et al. | |
| 9,045,847 B2 | 6/2015 | Batchvarova et al. | |
| 9,050,452 B2 | 6/2015 | Sun et al. | |
| 9,052,533 B2 | 6/2015 | Pugh et al. | |
| 9,056,282 B2 | 6/2015 | Miller et al. | |
| 9,062,180 B2 | 6/2015 | Scales et al. | |
| 9,067,811 B1 | 6/2015 | Bennett et al. | |
| 9,070,615 B2 | 6/2015 | Elian et al. | |
| 9,075,009 B2 | 7/2015 | Kim et al. | |
| 9,080,267 B2 | 7/2015 | Batchvarova et al. | |
| 9,095,823 B2 | 8/2015 | Fleming et al. | |
| 9,096,050 B2 | 8/2015 | Bedell et al. | |
| 9,096,437 B2 | 8/2015 | Tour et al. | |
| 9,102,111 B2 | 8/2015 | Pugh et al. | |
| 9,108,158 B2 | 8/2015 | Yu et al. | |
| 9,110,310 B2 | 8/2015 | Pugh et al. | |
| 9,125,715 B2 | 9/2015 | Pugh et al. | |
| 9,134,546 B2 | 9/2015 | Pugh et al. | |
| 9,170,646 B2 | 10/2015 | Toner et al. | |
| 9,185,486 B2 | 11/2015 | Pugh | |
| 9,193,587 B2 | 11/2015 | Bennett et al. | |
| 9,195,075 B2 | 11/2015 | Pugh et al. | |
| 9,225,375 B2 | 12/2015 | Pugh et al. | |
| 9,388,048 B1 | 7/2016 | Zhou et al. | |
| 9,425,709 B2 | 8/2016 | Hayashi et al. | |
| 9,463,421 B2 | 10/2016 | Fleming | |
| 9,505,192 B2 | 11/2016 | Stoltenberg et al. | |
| 9,567,224 B2 | 2/2017 | Bedworth | |
| 9,572,918 B2 | 2/2017 | Bachmann et al. | |
| 9,592,475 B2 | 3/2017 | Stoltenberg et al. | |
| 9,610,546 B2 | 4/2017 | Sinton et al. | |
| 2001/0036556 A1 | 11/2001 | Jen | |
| 2001/0047157 A1 | 11/2001 | Burnett et al. | |
| 2001/0055597 A1 | 12/2001 | Liu et al. | |
| 2002/0079004 A1 | 6/2002 | Sato et al. | |
| 2002/0079054 A1 | 6/2002 | Nakatani | |
| 2002/0104435 A1 | 8/2002 | Baker et al. | |
| 2002/0115957 A1 | 8/2002 | Sun et al. | |
| 2002/0183682 A1 | 12/2002 | Darvish et al. | |
| 2002/0183686 A1 | 12/2002 | Darvish et al. | |
| 2003/0052354 A1 | 3/2003 | Dennison | |
| 2003/0134281 A1 | 7/2003 | Evans | |
| 2003/0138777 A1 | 7/2003 | Evans | |
| 2003/0146221 A1 | 8/2003 | Lauer et al. | |
| 2003/0159985 A1 | 8/2003 | Siwy et al. | |
| 2004/0061253 A1 | 4/2004 | Kleinmeyer et al. | |
| 2004/0063097 A1 | 4/2004 | Evans | |
| 2004/0099324 A1 | 5/2004 | Fraser et al. | |
| 2004/0111968 A1 | 6/2004 | Day et al. | |
| 2004/0112865 A1 | 6/2004 | McCullough et al. | |
| 2004/0121488 A1 | 6/2004 | Chang et al. | |
| 2004/0142463 A1 | 7/2004 | Walker et al. | |
| 2004/0185730 A1 | 9/2004 | Lambino et al. | |
| 2004/0193043 A1 | 9/2004 | Duchon et al. | |
| 2004/0199243 A1 | 10/2004 | Yodfat | |
| 2004/0217036 A1 | 11/2004 | Ginsberg et al. | |
| 2004/0241214 A1 | 12/2004 | Kirkwood et al. | |
| 2004/0251136 A1 | 12/2004 | Lean et al. | |
| 2005/0004508 A1 | 1/2005 | Sun et al. | |
| 2005/0004509 A1 | 1/2005 | Sun et al. | |
| 2005/0004550 A1 | 1/2005 | Sun et al. | |
| 2005/0010161 A1 | 1/2005 | Sun et al. | |
| 2005/0010192 A1 | 1/2005 | Sun et al. | |
| 2005/0015042 A1 | 1/2005 | Sun et al. | |
| 2005/0053563 A1 | 3/2005 | Manissier et al. | |
| 2005/0112078 A1 | 5/2005 | Boddupalli et al. | |
| 2005/0126966 A1 | 6/2005 | Tanida et al. | |
| 2005/0129633 A1 | 6/2005 | Lin | |
| 2005/0148996 A1 | 7/2005 | Sun et al. | |
| 2005/0170089 A1 | 8/2005 | Lashmore et al. | |
| 2005/0189673 A1 | 9/2005 | Klug et al. | |
| 2005/0226834 A1 | 10/2005 | Lambino et al. | |
| 2005/0238730 A1 | 10/2005 | Le Fur et al. | |
| 2006/0005381 A1 | 1/2006 | Nishi et al. | |
| 2006/0036332 A1 | 2/2006 | Jennings | |
| 2006/0073370 A1 | 4/2006 | Krusic et al. | |
| 2006/0093885 A1 | 5/2006 | Krusic et al. | |
| 2006/0121279 A1 | 6/2006 | Petrik | |
| 2006/0151382 A1 | 7/2006 | Petrik | |
| 2006/0166347 A1 * | 7/2006 | Faulstich | C12N 1/06 435/259 |
| 2006/0180604 A1 | 8/2006 | Ginsberg et al. | |
| 2006/0222701 A1 | 10/2006 | Kulkarni et al. | |
| 2006/0253078 A1 | 11/2006 | Wu et al. | |
| 2007/0004640 A1 | 1/2007 | Lin et al. | |
| 2007/0032054 A1 | 2/2007 | Ramaswamy et al. | |
| 2007/0056894 A1 | 3/2007 | Connors, Jr. | |
| 2007/0060862 A1 | 3/2007 | Sun et al. | |
| 2007/0062856 A1 | 3/2007 | Pahl et al. | |
| 2007/0099813 A1 | 5/2007 | Luizzi et al. | |
| 2007/0131646 A1 | 6/2007 | Donnelly et al. | |
| 2007/0284279 A1 | 12/2007 | Doskoczynski et al. | |
| 2008/0017564 A1 | 1/2008 | Hammond | |
| 2008/0035484 A1 | 2/2008 | Wu et al. | |
| 2008/0035541 A1 | 2/2008 | Franzreb et al. | |
| 2008/0045877 A1 | 2/2008 | Levin et al. | |
| 2008/0061477 A1 | 3/2008 | Capizzo | |
| 2008/0063585 A1 | 3/2008 | Smalley et al. | |
| 2008/0081323 A1 | 4/2008 | Keeley et al. | |
| 2008/0081362 A1 | 4/2008 | Keeley et al. | |
| 2008/0149561 A1 | 6/2008 | Chu et al. | |
| 2008/0156648 A1 | 7/2008 | Dudziak et al. | |
| 2008/0170982 A1 | 7/2008 | Zhang et al. | |
| 2008/0185293 A1 | 8/2008 | Klose et al. | |
| 2008/0188836 A1 | 8/2008 | Weber et al. | |
| 2008/0190508 A1 | 8/2008 | Booth et al. | |
| 2008/0241085 A1 | 10/2008 | Lin et al. | |
| 2008/0268016 A1 | 10/2008 | Fang et al. | |
| 2008/0290020 A1 | 11/2008 | Marand et al. | |
| 2008/0290111 A1 | 11/2008 | Ginsberg et al. | |
| 2009/0023572 A1 | 1/2009 | Backes et al. | |
| 2009/0039019 A1 | 2/2009 | Raman | |

(56) References Cited

U.S. PATENT DOCUMENTS

| | | |
|---|---|---|
| 2009/0048685 A1 | 2/2009 | Frigstad et al. |
| 2009/0075371 A1 | 3/2009 | Keeley et al. |
| 2009/0087395 A1 | 4/2009 | Lin et al. |
| 2009/0117335 A1 | 5/2009 | Iyoda et al. |
| 2009/0148495 A1 | 6/2009 | Hammer et al. |
| 2009/0176159 A1 | 7/2009 | Zhamu et al. |
| 2009/0222072 A1 | 9/2009 | Robinson et al. |
| 2009/0236295 A1 | 9/2009 | Braun et al. |
| 2009/0241242 A1 | 10/2009 | Beatty et al. |
| 2009/0283475 A1 | 11/2009 | Hylton et al. |
| 2009/0291270 A1 | 11/2009 | Zettl et al. |
| 2009/0294300 A1 | 12/2009 | Kanzius et al. |
| 2009/0306364 A1 | 12/2009 | Beer et al. |
| 2010/0000754 A1 | 1/2010 | Mann et al. |
| 2010/0016778 A1 | 1/2010 | Chattopadhyay |
| 2010/0021708 A1 | 1/2010 | Kong et al. |
| 2010/0024722 A1 | 2/2010 | Ochs et al. |
| 2010/0024838 A1 | 2/2010 | Ochs et al. |
| 2010/0025330 A1 | 2/2010 | Ratto et al. |
| 2010/0055464 A1 | 3/2010 | Sung |
| 2010/0059378 A1 | 3/2010 | Elson et al. |
| 2010/0072643 A1 | 3/2010 | Pugh et al. |
| 2010/0076553 A1 | 3/2010 | Pugh et al. |
| 2010/0105834 A1 | 4/2010 | Tour et al. |
| 2010/0110372 A1 | 5/2010 | Pugh et al. |
| 2010/0124564 A1 | 5/2010 | Martinson et al. |
| 2010/0127312 A1 | 5/2010 | Grebel et al. |
| 2010/0161014 A1 | 6/2010 | Lynch et al. |
| 2010/0167551 A1 | 7/2010 | Dedontney |
| 2010/0196439 A1 | 8/2010 | Beck et al. |
| 2010/0209515 A1 | 8/2010 | Chantalat et al. |
| 2010/0213079 A1 | 8/2010 | Willis |
| 2010/0224555 A1 | 9/2010 | Hoek et al. |
| 2010/0228204 A1 | 9/2010 | Beatty et al. |
| 2010/0233781 A1 | 9/2010 | Bangera et al. |
| 2010/0249273 A1 | 9/2010 | Scales et al. |
| 2010/0258111 A1 | 10/2010 | Shah et al. |
| 2010/0323177 A1 | 12/2010 | Ruoff et al. |
| 2010/0327847 A1 | 12/2010 | Leiber et al. |
| 2011/0014217 A1 | 1/2011 | Fahmy et al. |
| 2011/0037033 A1 | 2/2011 | Green et al. |
| 2011/0041519 A1 | 2/2011 | McAlister |
| 2011/0041687 A1 | 2/2011 | Diaz et al. |
| 2011/0045523 A1 | 2/2011 | Strano et al. |
| 2011/0054418 A1 | 3/2011 | Pugh et al. |
| 2011/0054576 A1 | 3/2011 | Robinson et al. |
| 2011/0056892 A1 | 3/2011 | Lancaster |
| 2011/0073563 A1 | 3/2011 | Chang et al. |
| 2011/0092054 A1 | 4/2011 | Seo et al. |
| 2011/0092949 A1 | 4/2011 | Wang |
| 2011/0100921 A1* | 5/2011 | Heinrich ............ A61M 1/1081 210/670 |
| 2011/0112484 A1 | 5/2011 | Carter et al. |
| 2011/0118655 A1 | 5/2011 | Fassih et al. |
| 2011/0120970 A1 | 5/2011 | Joo et al. |
| 2011/0124253 A1 | 5/2011 | Shah et al. |
| 2011/0139707 A1 | 6/2011 | Siwy et al. |
| 2011/0152795 A1 | 6/2011 | Aledo et al. |
| 2011/0201201 A1 | 8/2011 | Arnold et al. |
| 2011/0202201 A1 | 8/2011 | Matsubara |
| 2011/0253630 A1 | 10/2011 | Bakajin et al. |
| 2011/0258791 A1 | 10/2011 | Batchvarova et al. |
| 2011/0258796 A1 | 10/2011 | Batchvarova et al. |
| 2011/0262645 A1 | 10/2011 | Batchvarova et al. |
| 2011/0263912 A1 | 10/2011 | Miller et al. |
| 2011/0269920 A1 | 11/2011 | Min et al. |
| 2012/0031833 A1 | 2/2012 | Ho et al. |
| 2012/0048804 A1 | 3/2012 | Stetson et al. |
| 2012/0116228 A1 | 5/2012 | Okubo |
| 2012/0145548 A1 | 6/2012 | Sivan et al. |
| 2012/0148633 A1 | 6/2012 | Sun et al. |
| 2012/0162600 A1 | 6/2012 | Pugh et al. |
| 2012/0183738 A1 | 7/2012 | Zettl et al. |
| 2012/0186850 A1 | 7/2012 | Sugiyama et al. |
| 2012/0211367 A1 | 8/2012 | Vecitis |
| 2012/0218508 A1 | 8/2012 | Pugh et al. |
| 2012/0220053 A1 | 8/2012 | Lee et al. |
| 2012/0234453 A1 | 9/2012 | Pugh et al. |
| 2012/0234679 A1 | 9/2012 | Garaj et al. |
| 2012/0235277 A1 | 9/2012 | Pugh et al. |
| 2012/0236254 A1 | 9/2012 | Pugh et al. |
| 2012/0236524 A1 | 9/2012 | Pugh et al. |
| 2012/0241371 A1 | 9/2012 | Revanur et al. |
| 2012/0242953 A1 | 9/2012 | Pugh et al. |
| 2012/0255899 A1 | 10/2012 | Choi et al. |
| 2012/0267337 A1 | 10/2012 | Striemer et al. |
| 2012/0292245 A1 | 11/2012 | Saito |
| 2012/0298396 A1 | 11/2012 | Hong et al. |
| 2012/0301707 A1 | 11/2012 | Kinloch et al. |
| 2013/0015136 A1 | 1/2013 | Bennett et al. |
| 2013/0034760 A1 | 2/2013 | Otts et al. |
| 2013/0045523 A1* | 2/2013 | Leach ................ B01F 13/0023 435/214 |
| 2013/0056367 A1 | 3/2013 | Martinez et al. |
| 2013/0071941 A1 | 3/2013 | Miller |
| 2013/0096292 A1 | 4/2013 | Brahmasandra et al. . 536/25.41 |
| 2013/0100436 A1 | 4/2013 | Jackson et al. |
| 2013/0105417 A1* | 5/2013 | Stetson .................. C02F 1/442 210/806 |
| 2013/0108839 A1 | 5/2013 | Arnold et al. |
| 2013/0116541 A1 | 5/2013 | Gracias et al. |
| 2013/0131214 A1 | 5/2013 | Scales et al. |
| 2013/0135578 A1 | 5/2013 | Pugh et al. |
| 2013/0146221 A1 | 6/2013 | Kolmakov et al. |
| 2013/0146480 A1 | 6/2013 | Garaj et al. |
| 2013/0152386 A1 | 6/2013 | Pandojirao-S et al. |
| 2013/0174978 A1 | 7/2013 | Pugh et al. |
| 2013/0190476 A1 | 7/2013 | Lancaster et al. |
| 2013/0192460 A1 | 8/2013 | Miller et al. |
| 2013/0192461 A1 | 8/2013 | Miller et al. |
| 2013/0194540 A1 | 8/2013 | Pugh et al. |
| 2013/0213568 A1 | 8/2013 | Pugh et al. |
| 2013/0215377 A1 | 8/2013 | Pugh et al. |
| 2013/0215378 A1 | 8/2013 | Pugh et al. |
| 2013/0215380 A1 | 8/2013 | Pugh et al. |
| 2013/0216581 A1 | 8/2013 | Fahmy et al. |
| 2013/0240355 A1 | 9/2013 | Ho et al. |
| 2013/0240437 A1 | 9/2013 | Rodrigues et al. |
| 2013/0248097 A1 | 9/2013 | Ploss, Jr. |
| 2013/0248367 A1 | 9/2013 | Stetson et al. |
| 2013/0249147 A1 | 9/2013 | Bedworth |
| 2013/0256118 A1 | 10/2013 | Meller et al. |
| 2013/0256139 A1 | 10/2013 | Peng |
| 2013/0256154 A1 | 10/2013 | Peng |
| 2013/0256210 A1 | 10/2013 | Fleming |
| 2013/0256211 A1 | 10/2013 | Fleming |
| 2013/0261568 A1 | 10/2013 | Martinson et al. |
| 2013/0269819 A1 | 10/2013 | Ruby et al. |
| 2013/0270188 A1 | 10/2013 | Karnik et al. |
| 2013/0273288 A1 | 10/2013 | Luo et al. |
| 2013/0277305 A1 | 10/2013 | Stetson et al. |
| 2013/0295150 A1 | 11/2013 | Chantalat et al. |
| 2013/0309776 A1 | 11/2013 | Drndic et al. |
| 2013/0317131 A1 | 11/2013 | Scales et al. |
| 2013/0317132 A1 | 11/2013 | Scales et al. |
| 2013/0317133 A1 | 11/2013 | Scales et al. |
| 2013/0323295 A1 | 12/2013 | Scales et al. |
| 2013/0338611 A1 | 12/2013 | Pugh et al. |
| 2013/0338744 A1 | 12/2013 | Frewin et al. |
| 2014/0002788 A1 | 1/2014 | Otts et al. |
| 2014/0005514 A1 | 1/2014 | Pugh et al. |
| 2014/0015160 A1 | 1/2014 | Kung et al. |
| 2014/0017322 A1 | 1/2014 | Dai et al. |
| 2014/0048411 A1 | 2/2014 | Choi et al. |
| 2014/0066958 A1 | 3/2014 | Priewe |
| 2014/0079936 A1 | 3/2014 | Russo et al. |
| 2014/0093728 A1 | 4/2014 | Shah et al. |
| 2014/0128891 A1 | 5/2014 | Astani-Matthies et al. |
| 2014/0141521 A1 | 5/2014 | Peng et al. |
| 2014/0151288 A1 | 6/2014 | Miller et al. |
| 2014/0151631 A1 | 6/2014 | Duesberg et al. |
| 2014/0154464 A1 | 6/2014 | Miller et al. |
| 2014/0170195 A1 | 6/2014 | Fassih et al. |
| 2014/0171541 A1 | 6/2014 | Scales et al. |

(56) References Cited

U.S. PATENT DOCUMENTS

| | | |
|---|---|---|
| 2014/0174927 A1 | 6/2014 | Bashir et al. |
| 2014/0190004 A1 | 7/2014 | Riall et al. |
| 2014/0190550 A1 | 7/2014 | Loh et al. |
| 2014/0190676 A1 | 7/2014 | Zhamu et al. |
| 2014/0190833 A1 | 7/2014 | Lieber et al. |
| 2014/0192313 A1 | 7/2014 | Riall et al. |
| 2014/0192314 A1 | 7/2014 | Riall et al. |
| 2014/0199777 A2 | 7/2014 | Ruiz et al. |
| 2014/0209539 A1 | 7/2014 | El Badawi et al. |
| 2014/0212596 A1 | 7/2014 | Jahangiri-Famenini |
| 2014/0230653 A1 | 8/2014 | Yu et al. |
| 2014/0230733 A1 | 8/2014 | Miller |
| 2014/0231351 A1 | 8/2014 | Wickramasinghe et al. |
| 2014/0248621 A1 | 9/2014 | Collins |
| 2014/0257348 A1 | 9/2014 | Priewe et al. |
| 2014/0257517 A1 | 9/2014 | Deichmann et al. |
| 2014/0259657 A1 | 9/2014 | Riall et al. |
| 2014/0261999 A1 | 9/2014 | Stetson et al. |
| 2014/0263035 A1 | 9/2014 | Stoltenberg et al. |
| 2014/0263178 A1 | 9/2014 | Sinton et al. |
| 2014/0264977 A1 | 9/2014 | Pugh et al. |
| 2014/0268015 A1 | 9/2014 | Riall et al. |
| 2014/0268020 A1 | 9/2014 | Pugh et al. |
| 2014/0268021 A1 | 9/2014 | Pugh et al. |
| 2014/0268026 A1 | 9/2014 | Pugh et al. |
| 2014/0272286 A1 | 9/2014 | Stoltenberg et al. |
| 2014/0272522 A1 | 9/2014 | Pugh et al. |
| 2014/0273315 A1 | 9/2014 | Pugh et al. |
| 2014/0273316 A1 | 9/2014 | Pugh et al. |
| 2014/0276481 A1 | 9/2014 | Pugh et al. |
| 2014/0276999 A1 | 9/2014 | Harms et al. |
| 2014/0306361 A1 | 10/2014 | Pugh et al. |
| 2014/0308681 A1 | 10/2014 | Strano et al. |
| 2014/0315213 A1 | 10/2014 | Nagrath et al. |
| 2014/0318373 A1 | 10/2014 | Wood et al. |
| 2014/0322518 A1 | 10/2014 | Addleman et al. |
| 2014/0333892 A1 | 11/2014 | Pugh et al. |
| 2014/0335661 A1 | 11/2014 | Pugh et al. |
| 2014/0343580 A1 | 11/2014 | Priewe |
| 2014/0346081 A1 | 11/2014 | Sowden et al. |
| 2014/0349892 A1 | 11/2014 | Van Der Zaag et al. |
| 2014/0350372 A1 | 11/2014 | Pugh et al. |
| 2014/0377651 A1 | 12/2014 | Kwon et al. |
| 2014/0377738 A1 | 12/2014 | Bachmann et al. |
| 2015/0015843 A1 | 1/2015 | Pugh et al. |
| 2015/0017918 A1 | 1/2015 | Pugh et al. |
| 2015/0057762 A1 | 2/2015 | Harms et al. |
| 2015/0061990 A1 | 3/2015 | Toner et al. |
| 2015/0062533 A1 | 3/2015 | Toner et al. |
| 2015/0063605 A1 | 3/2015 | Pugh |
| 2015/0066063 A1 | 3/2015 | Priewe |
| 2015/0075667 A1 | 3/2015 | McHugh et al. |
| 2015/0077658 A1 | 3/2015 | Pugh et al. |
| 2015/0077659 A1 | 3/2015 | Pugh et al. |
| 2015/0077660 A1 | 3/2015 | Pugh et al. |
| 2015/0077661 A1 | 3/2015 | Pugh et al. |
| 2015/0077662 A1 | 3/2015 | Pugh et al. |
| 2015/0077663 A1 | 3/2015 | Pugh et al. |
| 2015/0077699 A1 | 3/2015 | De Sio et al. |
| 2015/0077702 A9 | 3/2015 | Pugh et al. |
| 2015/0079683 A1 | 3/2015 | Yager et al. |
| 2015/0087249 A1 | 3/2015 | Pugh et al. |
| 2015/0096935 A1 | 4/2015 | Mitra et al. |
| 2015/0098910 A1 | 4/2015 | Mordas et al. |
| 2015/0101931 A1 | 4/2015 | Garaj et al. |
| 2015/0105686 A1 | 4/2015 | Vasan |
| 2015/0118318 A1 | 4/2015 | Fahmy et al. |
| 2015/0122727 A1 | 5/2015 | Karnik et al. |
| 2015/0138454 A1 | 5/2015 | Pugh et al. |
| 2015/0142107 A1 | 5/2015 | Pugh et al. |
| 2015/0145155 A1 | 5/2015 | Pugh et al. |
| 2015/0146162 A1 | 5/2015 | Pugh et al. |
| 2015/0147474 A1 | 5/2015 | Batchvarova et al. |
| 2015/0170788 A1 | 6/2015 | Miller et al. |
| 2015/0174253 A1 | 6/2015 | Sun et al. |
| 2015/0174254 A1 | 6/2015 | Sun et al. |
| 2015/0182473 A1 | 7/2015 | Bosnyak et al. |
| 2015/0185180 A1 | 7/2015 | Ruhl et al. |
| 2015/0196579 A1 | 7/2015 | Ferrante et al. |
| 2015/0202351 A1 | 7/2015 | Kaplan et al. |
| 2015/0212339 A1 | 7/2015 | Pugh et al. |
| 2015/0217219 A1 | 8/2015 | Sinsabaugh et al. |
| 2015/0218210 A1 | 8/2015 | Stetson et al. |
| 2015/0221474 A1 | 8/2015 | Bedworth et al. |
| 2015/0231557 A1 | 8/2015 | Miller et al. |
| 2015/0231577 A1 | 8/2015 | Nair et al. |
| 2015/0247178 A1 | 9/2015 | Mountcastle et al. |
| 2015/0258254 A1 | 9/2015 | Simon et al. |
| 2015/0258498 A1 | 9/2015 | Simon et al. |
| 2015/0258502 A1 | 9/2015 | Turowski et al. |
| 2015/0258503 A1 | 9/2015 | Sinton et al. |
| 2015/0258525 A1 | 9/2015 | Westman et al. |
| 2015/0268150 A1 | 9/2015 | Newkirk et al. |
| 2015/0272834 A1 | 10/2015 | Sun et al. |
| 2015/0272896 A1 | 10/2015 | Sun et al. |
| 2015/0273401 A1 | 10/2015 | Miller et al. |
| 2015/0309337 A1 | 10/2015 | Flitsch et al. |
| 2015/0321147 A1 | 11/2015 | Fleming et al. |
| 2015/0321149 A1 | 11/2015 | McGinnis |
| 2015/0323811 A1 | 11/2015 | Flitsch et al. |
| 2015/0336202 A1 | 11/2015 | Bedworth et al. |
| 2015/0342900 A1 | 12/2015 | Putnins |
| 2015/0346382 A1 | 12/2015 | Bliven et al. |
| 2015/0351887 A1 | 12/2015 | Peters |
| 2015/0359742 A1 | 12/2015 | Fassih et al. |
| 2015/0378176 A1 | 12/2015 | Flitsch et al. |
| 2016/0009049 A1 | 1/2016 | Stoltenberg et al. |
| 2016/0038885 A1 | 2/2016 | Hogen-Esch et al. |
| 2016/0043384 A1 | 2/2016 | Zhamu et al. |
| 2016/0058932 A1 | 3/2016 | Stetson et al. |
| 2016/0059190 A1 | 3/2016 | Yoo et al. |
| 2016/0067390 A1 | 3/2016 | Simon et al. |
| 2016/0074814 A1 | 3/2016 | Park et al. |
| 2016/0074815 A1 | 3/2016 | Sinton et al. |
| 2016/0272499 A1 | 9/2016 | Zurutuza Elorza et al. |
| 2016/0282326 A1 | 9/2016 | Waduge et al. |
| 2016/0284811 A1 | 9/2016 | Yu et al. |
| 2016/0339160 A1 | 11/2016 | Bedworth et al. |
| 2017/0032962 A1 | 2/2017 | Zurutuza Elorza et al. |
| 2017/0037356 A1 | 2/2017 | Simon et al. |
| 2017/0057812 A1 | 3/2017 | Zurutuza Elorza et al. |

FOREIGN PATENT DOCUMENTS

| | | | |
|---|---|---|---|
| CN | 1128501 A | 8/1996 | |
| CN | 101108194 A | 1/2008 | |
| CN | 101243544 | 8/2008 | |
| CN | 101428198 A | 5/2009 | |
| CN | 101489653 A | 7/2009 | |
| CN | 101996853 A | 3/2011 | |
| CN | 102242062 A | 11/2011 | |
| CN | 102344132 | 2/2012 | |
| CN | 102423272 | 4/2012 | |
| CN | 102592720 A | 7/2012 | |
| CN | 101996853 B | 8/2012 | |
| CN | 102637584 A | 8/2012 | |
| CN | 103153441 | 6/2013 | |
| CN | 103182249 A | 7/2013 | |
| CN | 103603706 A | 2/2014 | |
| DE | 19536560 | 3/1997 | |
| DE | 10 2005 049 388 A1 | 4/2007 | |
| EP | 0 364 628 A1 | 4/1990 | |
| EP | 1 034 251 | 1/2004 | |
| EP | 1 777 250 A1 | 4/2007 | |
| EP | 1 872 812 | 1/2008 | |
| EP | 2 060 286 | 5/2009 | |
| EP | 2107120 A1 | 10/2009 | ............ C12Q 1/24 |
| EP | 2 230 511 A1 | 9/2010 | |
| EP | 1 603 609 | 5/2011 | |
| EP | 2 354 272 | 8/2011 | |
| EP | 2 450 096 | 5/2012 | |

(56) References Cited

FOREIGN PATENT DOCUMENTS

| | | | |
|---|---|---|---|
| EP | 2 489 520 | 8/2012 | |
| EP | 2 511 002 | 10/2012 | |
| EP | 2 586 473 | 5/2013 | |
| EP | 2 679 540 | 1/2014 | |
| EP | 2 937 313 | 10/2015 | |
| EP | 3 070 053 | 9/2016 | |
| EP | 3 084 398 | 10/2016 | |
| EP | 1 538 2430.5 | 3/2017 | |
| EP | 3 135 631 | 3/2017 | |
| JP | 59-102111 | 7/1984 | |
| JP | 10-510471 | 5/1995 | |
| JP | 7504120 | 5/1995 | |
| JP | 2001-232158 | 8/2001 | |
| JP | 2004-179014 | 6/2004 | |
| JP | 2005-126966 | 5/2005 | |
| JP | 2006-188393 | 7/2006 | |
| JP | 2011-168448 A | 9/2011 | |
| JP | 2011-241479 | 12/2011 | |
| JP | 2004-202480 | 7/2014 | |
| JP | 2015-503405 | 2/2015 | |
| JP | 2016-175828 | 10/2016 | |
| KR | 1020110084110 | 7/2011 | |
| KR | 10-2012-0022164 A | 3/2012 | |
| KR | 1020120022164 A | 3/2012 | |
| KR | 1020140002570 | 1/2014 | |
| WO | WO-93/33901 | 3/1993 | |
| WO | WO-93/12859 | 8/1993 | |
| WO | WO-95/00231 | 1/1995 | |
| WO | WO-97/12664 A1 | 4/1997 | |
| WO | WO-98/30501 A2 | 7/1998 | |
| WO | WO 00/70012 | 11/2000 | ............ C12M 1/40 |
| WO | WO-02/055539 A1 | 7/2002 | |
| WO | WO-2013/115762 | 8/2003 | |
| WO | WO 2004/009840 A1 | 1/2004 | ............ C12Q 1/24 |
| WO | WO-2004/082733 | 9/2004 | |
| WO | WO-2005/047857 A2 | 5/2005 | |
| WO | WO-2007/103411 A2 | 9/2007 | |
| WO | WO-2007/140252 A1 | 12/2007 | |
| WO | WO-2008/008533 | 1/2008 | |
| WO | WO-2009/129984 A1 | 10/2009 | |
| WO | WO-2010/006080 | 1/2010 | |
| WO | WO-2010/115904 A1 | 10/2010 | |
| WO | WO-2011/019686 A1 | 2/2011 | |
| WO | WO-2011/046706 A1 | 4/2011 | |
| WO | WO-2011/001674 | 6/2011 | |
| WO | WO-2011/063458 A1 | 6/2011 | |
| WO | WO-2011/075158 | 6/2011 | |
| WO | WO-2011/094204 A2 | 8/2011 | |
| WO | WO 2011/100458 A2 | 8/2011 | ............ G01N 33/48 |
| WO | WO-2011/138689 A2 | 11/2011 | |
| WO | WO-2012/006657 A1 | 1/2012 | |
| WO | WO 2012/012801 A2 | 1/2012 | ........... G01N 33/574 |
| WO | WO-2012/021801 A2 | 2/2012 | |
| WO | WO-2012/027148 A1 | 3/2012 | |
| WO | WO-2012/028695 | 3/2012 | |
| WO | WO-2012/030368 A1 | 3/2012 | |
| WO | WO-2012/125770 | 9/2012 | |
| WO | WO-2012/138671 A2 | 10/2012 | |
| WO | WO-2012/142852 A1 | 10/2012 | |
| WO | WO-2013/016445 A1 | 1/2013 | |
| WO | WO-2013/048063 A1 | 4/2013 | |
| WO | WO-2013/138137 A1 | 9/2013 | |
| WO | WO-2013/138698 A1 | 9/2013 | |
| WO | WO-2013/151799 | 10/2013 | |
| WO | WO 2013/152179 A1 | 10/2013 | ........... A61M 5/165 |
| WO | WO-2014/084861 A1 | 6/2014 | |
| WO | WO-2014/168629 A1 | 10/2014 | |
| WO | PCT/US2015/018114 | 2/2015 | |
| WO | WO-2015/030698 A1 | 3/2015 | |
| WO | PCT/US2015/028948 | 5/2015 | |
| WO | WO-2015/138736 A1 | 9/2015 | |
| WO | WO-2015/138752 A1 | 9/2015 | |
| WO | WO-2015/1138771 A1 | 9/2015 | |
| WO | WO-2015/197217 | 12/2015 | |
| WO | WO-2016/102003 | 6/2016 | |

OTHER PUBLICATIONS

CN Office Action in Chinese Application No. 201380013988.9 dated Aug. 18, 2016 (English translation not readily available).
Cohen-Tanugi, "Nanoporous graphene as a water desalination membrane," (Ph.D. Thesis, Massachusetts Institute of Technology) (Jun. 2015).
U.S. Notice of Allowance in U.S. Appl. No. 14/610,770 dated Aug. 12, 2016.
U.S. Office Action in U.S. Appl. No. 14/656,190 dated Aug. 29, 2016.
U.S. Office Action for U.S. Appl. No. 14/656,580 dated Jun. 2, 2016.
U.S. Office Action in U.S. Appl. No. 14/819,273 dated Jul. 6, 2016.
U.S. Office Action for U.S. Appl. No. 14/856,198 dated Jun. 3, 2016.
Yoon, "Simulations show how to turn graphene's defects into assets," ScienceDaily (Oct. 4, 2016), www.sciencedaily.com/releases/2016/10/161004120428.htm.
Zabihi et al., "Formation of nanopore in a suspended graphene sheet with argon cluster bombardment: A molecular dynamics simulation study," Nuclear Instruments and Methods in Physics Research B, 343: 48-51: (Jan. 2015) (available online Nov. 2014).
Zhang et al. Modern Thin-Film Technology 284-285 (Metallurgical Industry Press, 1st ed. 2009) (English translation not readily available).
Zhao et al. (2012), "Effect of $SiO_2$ substrate on the irradiation-assisted manipulation of supported graphene: a molecular dynamics study," Nanotechnology 23(28): 285703 (Jul. 2012) (available online Jun. 2012).
Zhao et al. (May 2012), "Drilling Nanopores in Graphene with Clusters: A Molecular Dynamics Study," J. Phys. Chem. C, 116(21): 11776-11178 (2012) (available online May 2012).
Adiga et al., "Nanoporous Materials for Biomedical Devices," JOM 60: 26-32 (Mar. 25, 2008).
Allen et al., "Craters on silicon surfaces created by gas cluster ion impacts," Journal of Applied Physics, 92(7): 3671-8 (Oct. 2002).
AMI Applied Membranes Inc. (undated). FilmTec Nanofiltration Membrane Elements. Retrieved Jun. 1, 2016, from http://www.appliedmembranes.com/filmtec-nanofiltration-membrane-elements.html.
Apel, "Track etching technique in membrane technology," Radiation Measurements 34(1-6): 559-566 (Jun. 2001).
Atmeh et al., "Albumin Aggregates: Hydrodynamic Shape and Physico-Chemical Properties," Jordan Journal of Chemistry, 2(2): 169-182 (2007).
Bae et al., "Roll-to-roll production of 30-inch graphene films for transparent electrodes," Nature Nanotechnology 5: 574-578 (Jun. 20, 2010).
Bai et al., "Graphene nanomesh," Nature Nanotechnology 5: 190-194 (Feb. 14, 2010).
Baker. (2004). "Track-etch Membranes." In Membrane Technology and Applications (2nd ed., pp. 92-94). West Sussex, England: John Wiley & Sons.
Butler et al. "Progress, Challenges, and Opportunities in Two-Dimensional Materials Beyond Graphene", Materials Review 7(4): 2898-2926 (Mar. 6, 2013).
Chen et al., "Mechanically Strong, Electrically Conductive, and Biocompatible Graphene Paper," Adv. Mater., 20(18): 3557-3561 (Sep. 2008) (available online Jul. 2008).
Chhowalla et al., "The chemistry of two-dimensional layered transition metal dichalcogenide nanosheets," Nature Chemistry 5: 263-275 (Mar. 20, 2013).
Childres et al., "Effect of oxygen plasma etching on graphene studied using Raman spectroscopy and electronic transport measurements," New Journal of Physics 13 (Feb. 10, 2011).
Clochard. (undated). Radiografted track-etched polymer membranes for research and application [Scholarly project]. In Laboratoire Des Solides Irradiés. Retrieved Jun. 2, 2016, from http://iramis.cea.fr/radiolyse/5juin2015/Clochard.pdf.
Cohen-Tanugi et al, "Water Desalination across Nanoporous Graphene," ACS Nano Letters 12(7): 3602-3608 (Jun. 5, 2012).

(56) References Cited

OTHER PUBLICATIONS

Colton, "Implantable biohybrid artificial organs," Cell Transplantation 4(4): 415-436 (Jul.-Aug. 1995).
Desai et al., "Nanoporous microsystems for islet cell replacement," Advanced Drug Delivery Reviews 56: 1661-1673 (Jul. 23, 2004).
Dong et al., "Growth of large-sized graphene thin-films by liquid precursor-based chemical vapor deposition under atmospheric pressure," Carbon 49(11): 3672-3678 (May 2011).
Fischbein et al., "Electron beam nanosculpting of suspended graphene sheets," Applied Physics Letters 93(113107): 1-3, (Sep. 16, 2008).
Fissell et al., "High-Performance Silicon Nanopore Hemofiltration Membranes," NIH-PA Author Manuscript, PMC, (Jan. 5, 2010), also published in J. Memb. Sci. 326(1): 58-63 (Jan. 5, 2009).
Fuertes et al., "Carbon composite membranes from Matrimid® and Kapton® polyimides for gas separation," Microporous and Mesoporous Materials, 33: 115-125 (Dec. 1999).
Galashev, "Computer study of the removal of Cu from the graphene surface using Ar clusters," Computational Materials Science, 98:123-128 (Feb. 2015) (available online Nov. 2014).
Gimi et al., "A Nanoporous, Transparent Microcontainer for Encapsulated Islet Therapy," J. Diabetes Sci. Tech. 3(2): 1-7 (Mar. 2009).
Hong et al., "Graphene multilayers as gates for multi-week sequential release of proteins from surfaces," NIH-PA Author Manuscript PMC (Jun. 1, 2014), also published in ACS Nano, Jan. 24, 2012; 6(1): 81-88 (first published online Dec. 29, 2011).
Hu et al., "Enabling graphene oxide nanosheets as water separation membranes," Environmental Science & Technology 47(8): 3715-3723 (Mar. 14, 2013).
International Search Report and Written Opinion in PCT/US2015/013599 dated Jul. 20, 2015.
International Search Report and Written Opinion in PCT/US2015/013805 dated Apr. 30, 2015.
International Search Report and Written Opinion in PCT/US2015/020246 dated Jun. 10, 2015.
International Search Report and Written Opinion in PCT/US2015/020296 dated Jun. 17, 2015.
International Search Report and Written Opinion in PCT/US2015/028948 dated Jul. 16, 2015.
International Search Report and Written Opinion in PCT/US2015/029932 dated Oct. 6, 2015.
International Search Report and Written Opinion in PCT/US2016/027607 dated Jul. 22, 2016.
International Search Report and Written Opinion in PCT/US2016/027616 dated Jul. 22, 2016.
International Search Report and Written Opinion in PCT/US2016/027596 dated Jul. 22, 2016.
International Search Report and Written Opinion in PCT/US2016/027603 dated Jul. 22, 2016.
International Search Report and Written Opinion in PCT/US2016/027610 dated Jul. 22, 2016.
International Search Report and Written Opinion in PCT/US2016/027612 dated Jul. 22, 2016.
International Search Report and Written Opinion in PCT/US2016/027637 dated Jun. 22, 2016.
International Search Report in PCT/US15/20201 dated Jun. 10, 2015.
International Search Report in PCT/US2015/048205 dated Dec. 4, 2015.
Inui et al., "Molecular dynamics simulations of nanopore processing in a graphene sheet by using gas cluster ion beam," Appl. Phys. A, 98: 787-794 (Mar. 2010) (available online Dec. 2009).
Jiang et al., "Porous Graphene as the Ultimate Membrane for Gas Separation," Nano Letters 9(12): 4019-4024 (Sep. 23, 2009).
Joshi et al., "Precise and ultrafast molecular sieving through graphene oxide membranes", Science 343(6172): 752-754 (Feb. 14, 2014).
Kanani et al., "Permeability—Selectivity Analysis for Ultrafiltration: Effect of Pore Geometry," NIH-PA Author Manuscript, PMC, (Mar. 1, 2011), also published in J. Memb. Sci. 349(1-2): 405 (Mar. 1, 2010).
Karan et al., "Ultrafast Viscous Permeation of Organic Solvents Through Diamond-Like Carbon Nanosheets," Science 335: 444-447 (Jan. 27, 2012).
Kim et al., "Fabrication and Characterization of Large Area, Semiconducting Nanoperforated Graphene Materials," Nano Letters 10(4): 1125-1131 (Mar. 1, 2010).
Kim et al., "The structural and electrical evolution of graphene by oxygen plasma-induced disorder," Nanotechnology IOP 20(375703): 1-8 (Aug. 26, 2009).
Koh et al., "Sensitive NMR Sensors Detect Antibodies to Influenza," NIH PA Author Manuscript PMC (Apr. 2009), also published in Angew. Chem. Int'l. Ed. Engl, 47(22): 4119-4121 (May 2008) (available online Apr. 2008).
Koski and Cui, "The New Skinny in Two-Dimensional Nanomaterials", ACS Nano 7(5): 3739-3743 (May 16, 2013).
Kurapati et al., "Graphene oxide based multilayer capsules with unique permeability properties: facile encapsulation of multiple drugs," Chemical Communication 48: 6013-6015 (Apr. 25, 2012).
Lehtinen et al., "Cutting and controlled modification of graphene with ion beams," Nanotechnology, 22: 175306 (8 pages) (Mar. 2011).
Li et al., "3D graphene oxide-polymer hydrogel: near-infrared light-triggered active scaffold for reversible cell capture and on-demand release," Advanced Materials 25: 6737-6743 (Oct. 7, 2013).
Liu et al., "Atomically Thin Molybdenum Disulfide Nanopores with High Sensitivity for DNA Translocation," ACS Nano 8(3): 2504-2511 (Feb. 18, 2014).
Liu et al., "Graphene Oxidation: Thickness-Dependent Etching and Strong Chemical Doping," Nano Letters 8(7): 1965-1970 (Jun. 19, 2008).
Marquardt et al., "Hybrid materials of platinum nanoparticles and thiol-functionalized graphene derivatives," Carbon 66: 285-294 (Jan. 2014; first published online Sep. 12, 2013).
Matteucci et al., "Chapter 1: Transport of gases and Vapors in Glass and Rubbery Polymers," in Materials Science of Membranes for Gas and Vapor Separation (Yampolskii et al eds. 2006) (available online Jun. 2006).
Mishra et al., "Functionalized Graphene Sheets for Arsenic Removal and Desalination of Sea Water," Desalination 282: 39-45 (Nov. 1, 2011).
Morse, "Scalable Synthesis of Semiconducting Nanopatterned Graphene Materials," InterNano Resources for Nanomanufacturing (undated). Retrieved Jun. 2, 2016 from: http://www.internano.org/node/345.
Nair et al., "Unimpeded Permeation of Water Through Helium-Leak-tight Graphene-Based Membranes," Science 335: 442-444 (Jan. 27, 2012).
Nam et al., "Monodispersed PtCo nanoparticles on hexadecyltrimethylammonium bromide treated graphene as an effective oxygen reduction reaction catalyst for proton exchange membrane fuel cells," Carbon 50: 3739-3747 (Aug. 2012) (available online Apr. 2012).
Nandamuri et al., "Chemical vapor deposition of graphene films," Nanotechnology 21(14): 1-4 (Mar. 10, 2010).
Nayini et al., "Synthesis and characterization of functionalized carbon nanotubes with different wetting behaviors and their influence on the wetting properties of carbon nanotubes/polymethylmethacrylate coatings," Progress in Organic Coatings, 77(6): 1007-1014 (Jun. 2014) (available online Mar. 2014).
O'Hern et al. "Selective Molecular Transport through Intrinsic Defects in a Single Layer of CVD Graphene," ACS Nano, 6(11): 10130-10138 (Oct. 2, 2012).
O'Hern et al., "Selective Ionic Transport through Tunable Subnanometer Pores in Single-Layer Graphene Membranes," Nano Letters 14(3): 1234-1241 (Feb. 3, 2014).
O'Hern, "Development of process to transfer large areas of LPCVD graphene from copper foil to a porous support substrate," 1-62 (M.S. Thesis, Massachusetts Institute of Technology) (Sep. 2011).

(56) References Cited

OTHER PUBLICATIONS

Paul, "Creating New Types of Carbon-Based Membranes," Science 335: 413-414 (Jan. 27, 2012).
Plant et al., "Size-dependent propagation of Au nanoclusters through few-layer graphene," Nanoscale, 6: 1258-1263 (2014) (available online Oct. 2013).
Popok. "Cluster Ion Implantation in Graphite and Diamond: Radiation Damage and Stopping of Cluster Constituents," Reviews on Advanced Materials Science 38(1): 7-16 (2014).
Russo et al., "Atom-by-atom nucleation and growth of graphene nanopores," PNAS, 109(16): 5953-5957 (Apr. 2012).
Schweicher et al., "Membranes to achieve immunoprotection of transplanted islets," NIH-PA Author Manuscript, PMC, (Nov. 13, 2014), also published in Frontiers in Bioscience (Landmark Ed) 19: 49-76 (Jan. 1, 2014).
Sint et al., "Selective Ion Passage through Functionalized Graphene Nanopores," JACS 130: 16448-16449 (Nov. 14, 2008).
Suk et al., "Water Transport Through Ultrathin Graphene," Journal of Physical Chemistry Letters 1(10): 1590-1594 (Apr. 30, 2010).
Sun et al., "Growth of graphene from solid carbon sources," Nature 468(7323): 549-552 (Nov. 25, 2010; including corrigendum in Nature 471(7336): 124 (Mar. 2011).
Tan et al., "Beta-cell regeneration and differentiation: how close are we to the 'holy grail'?" J. Mol. Encodrinol. 53(3): R119-R129 (Dec. 1, 2014).
Tang et al., "Highly wrinkled cross-linked graphene oxide membranes for biological and charge-storage applications," Small 8(3): 423-431 (Feb. 6, 2012; first published online Dec. 13, 2011).
Vlassiouk et al., "Versatile ultrathin nanoporous silicon nitride membranes," Proc. Natl. Acad. Sci. USA 106(50): 21039-21044 (Dec. 15, 2009).
Wadvalla, "Boosting agriculture through seawater," Nature Middle East (Jul. 2, 2012). Retrieved Jun. 1, 2016 from: natureasia.com/en/nmiddleeast/article/10.1038/nmiddleeast.2012.92?WT.mc_id=F BK NatureMEast].
Wikipedia, "Ion track." Jun. 1, 2016. Retrieved Jun. 1, 2016 from: en.wikipedia.org/wiki/ion_track.
Barreiro et al. "Understanding the catalyst-free transformation of amorphous carbon into graphene by current-induced annealing," Scientific Reports, 3 (Article 1115): 1-6 (Jan. 2013).
Botari et al., "Graphene healing mechanisms: A theoretical investigation," Carbon, 99: 302-309 (Apr. 2016) (published online Dec. 2015).
Chen et al., "Defect Scattering in Graphene," Physical Review Letters, 102: 236805-1-236805-4 (Jun. 2009).
Chen et al., "Self-healing of defected graphene," Applied Physics Letters, 102(10): 103107-1-103107-5 (Mar. 2013).
Cheng et al., "Ion Transport in Complex Layered Graphene-Based Membranes with Tuneable Interlayer Spacing," Science Advances, 2(2): e1501272 (9 pages) (Feb. 2016).
Crock et al., "Polymer Nanocomposites with Graphene-Based Hierarchical Fillers as Materials for Multifunctional Water Treatment Membranes," Water Research, 47(12): 3984-3996 (Aug. 2013) (published online Mar. 2013).
Han et al., "Ultrathin Graphene Nanofiltration Membrane for Water Purification," Advanced Functional Materials, 23(29): 3693-3700 (Aug. 2013).
International Search Report and Written Opinion in PCT/US2016/027583 dated Jan. 13, 2017.
Written Opinion in PCT/US2016/027590 dated Jan. 6, 2017.
International Search Report and Written Opinion in PCT/US2016/027594 dated Jan. 13, 2017.
International Search Report and Written Opinion in PCT/US2016/027628 dated Jan. 9, 2017.
International Search Report and Written Opinion in PCT/US2016/027631 dated Jan. 13, 2017.
International Search Report and Written Opinion in PCT/US2016/027632 dated Jan. 9, 2017.
Written Opinion in PCT/US2016/052010 dated Dec. 20, 2016.
International Search Report in PCT/US2016/027629 dated Dec. 8, 2016.
International Search Report in PCT/US2016/052007 dated Dec. 27, 2016.
Kjeldsen, T., "Yeast secretory expression of insulin precursors," Appl Microbiol Biotechnol, 54: 277-286 (May 2000).
Lin et al., "A Direct and Polymer-Free Method for Transferring Graphene Grown by Chemical Vapor Deposition to Any Substrate," ACSNANO, 8(2): 1784-1791 (Jan. 2014).
Liu et al. "Synthesis of high-quality monolayer and bilayer graphene on copper using chemical vapor deposition," Carbon, 49(13): 4122-4130 (Nov. 2011) (published online May 2011).
O'Hern et al., "Nanofiltration across defect-sealed nanoporous monolayer graphene," Nano Letters, 15(5): 3254-3260 (Apr. 2015).
U.S. Corrected Notice of Allowance in U.S. Appl. No. 13/480,569 dated May 26, 2015.
U.S. Notice of Allowance for U.S. Appl. No. 14/610,770 dated Apr. 25, 2016.
U.S. Notice of Allowance in U.S. Appl. No. 14/819,273 dated Dec. 14, 2016.
U.S. Notice of Allowance in U.S. Appl. No. 13/480,569 dated Feb. 27, 2015.
U.S. Office Action in U.S. Appl. No. 13/480,569 dated Jul. 30, 2014.
U.S. Office Action in U.S. Appl. No. 14/856,471 dated Dec. 1, 2016.
U.S. Restriction Requirement in U.S. Appl. No. 14/193,007 dated Jul. 17, 2015.
Wang et al., "Graphene Oxide Membranes with Tunable Permeability due to Embedded Carbon Dots," Chemical Communications, 50(86): 13089-13092 (Nov. 2014) (published online Sep. 2014).
Xu et al., "Graphene Oxide-$TiO_2$ Composite Filtration Membranes and their Potential Application for Water Purification," Carbon, 62: 465-471 (Oct. 2013) (published online Jun. 2013).
Zhao et al., "A glucose-responsive controlled release of insulin system based on enzyme multilayers-coated mesoporous silica particles," Chem. Commun., 47: 9459-9461 (Jun. 2011).
U.S. Notice of Allowance in U.S. Appl. No. 14/610,770 dated Jan. 23, 2017.
U.S. Notice of Allowance in U.S. Appl. No. 14/856,198 dated Feb. 10, 2017.
U.S. Notice of Allowance in U.S. Appl. No. 14/856,198 dated Mar. 1, 2017.
U.S. Office Action in U.S. Appl. No. 14/609,325 dated Feb. 16, 2017.
U.S. Office Action in U.S. Appl. No. 14/193,007 dated Mar. 23, 2017.
U.S. Office Action in U.S. Appl. No. 14/656,580 dated Feb. 9, 2017.
U.S. Office Action in U.S. Appl. No. 14/843,944 dated Jan. 6, 2017.
U.S. Office Action in U.S. Appl. No. 15/099,464 dated Mar. 10, 2017.
AE Search and Examination Report for United Arab Emirates Application No. P186/13 dated Oct. 4, 2016.
Agenor et al., "Renal tubular dysfunction in human visceral leishmaniasis (Kala-azar)," Clinical Nephrology 71(5): 492-500 (May 2009) (available online Mar. 21, 2011).
Albert et al., "Ringer's lactate is compatible with the rapid infusion of AS-3 preserved packed red blood cells," Can. J. Anaesth. 56(5): 352-356 (May 2009) (available online Apr. 2, 2009).
Aluru et al. "Modeling electronics on the nanoscale." Handbook of nanoscience, engineering and technology Goddard W, Brenner D, Lyshevski S, Iafrate GJ (2002): 11-1.
Alvarenga, "Carbon nanotube materials for aerospace wiring" Rochester Institute of Technology, 2010.
AMI Applied Membranes Inc., "Filmtec Nanofiltration Membrane Elements", Retrieved from appliedmembranes.com/nanofiltration_elements.htm, accessed Apr. 28, 2015 (2 Pages).
Aso et al., "Comparison of serum high-molecular weight (HMW) adiponectin with total adiponectin concentrations in type 2 diabetic patients with coronary artery using a novel enzyme-linked immunosorbent assay to detect HMW adiponectin," Diabetes 55(7): 1954-1960 (Jul. 2006).
AU Examination Report for Australian Patent Application No. 2013235234, dated Jan. 13, 2017, 4 pages.

(56) References Cited

OTHER PUBLICATIONS

AU Examination Report for Australian Patent Application No. 2013363283, dated Jun. 20, 2017, 4 pages.
AU Notice of Acceptance for Australian Application No. 2011293742 dated Jan. 13, 2016.
Axelsson et al., "Acute hyperglycemia induces rapid, reversible increases in glomerular permeability in nondiabetic rats," Am. J. Physiol. Renal Physiol. 298(6): F1306-F1312 (Jun. 2010) (available online Mar. 17, 2010).
Bains et al., "Novel lectins from rhizomes of two Acorus species with mitogenic activity and inhibitory potential towards murine cancer cell lines," Int'l Immunopharmacol. 5(9): 1470-1478 (Aug. 2005) (available online May 12, 2005).
Baker, "Membrane Technology and Applications", Membrane Technology and Applications; Apr. 14, 2004; pp. 92-94.
Barreiro et al. "Transport properties of graphene in the high-current limit." Physical review letters 103.7 (2009): 076601.
Bazargani et al. "Low molecular weight heparin improves peritoneal ultrafiltration and blocks complement and coagulation," Peritoneal Dialysis Int'l 25(4): 394-404 (Jul. 2005-Aug. 2005).
Bazargani, "Acute inflammation in peritoneal dialysis: experimental studies in rats. Characterization of regulatory mechanisms," Swedish Dental J. Supp. 171: 1-57, i (2005).
Beppu et al., "Antidiabetic effects of dietary administration of Aloe arborescens Miller components on multiple low-dose streptozotocin-induced diabetes in mice: investigation on hypoglycemic action and systemic absorption dynamics of aloe components," J. Ethnopharmacol. 103(3): 468-77 (Feb. 20, 2006) (available online Jan. 6, 2006).
Bieri et al. "Two-dimensional Polymer Formation on Surfaces: Insight into the Roles of Precursor Mobility and Reactivity" JACS, 2010, vol. 132, pp. 16669-16676.
Bruin et al., "Maturation and function of human embryonic stem cell-derived pancreatic progenitors in macroencapsulation devices following transplant into mice", Diabetologia (2013), vol. 56: 1987-1998 (Jun. 16, 2013).
Chu Ju, et al. "Modern Biotechnology" East China University of Technology Press, (Sep. 2007), vol. 1; pp. 306-307, ISBN 978-7-5628-2116-8.
Clochard, "Track-Etched Polymer Membranes," Laboratory of Irradiated Solids, Ecole Polytechnique, retrieved from http://www.lsi.polytechnique.fr/home/research/physics-and-chemistry-of-nano-objects/trac . . . , Accessed Jul. 30, 2015 (2 pages).
CN Notification of Grant for Chinese Application No. 201180049184.5 dated Jun. 6, 2016.
CN Office Action for Chinese Application No. 201380014845.X dated Jul. 8, 2016.
CN Office Action for Chinese Application No. 201380014845.X dated Sep. 2, 2015.
CN Office Action for Chinese Application No. 201380019165.5 dated Aug. 25, 2015.
CN Office Action for Chinese Application No. 201380073141.X dated Jun. 8, 2016.
CN Office Action for Chinese Application No. 201380073141.X dated Mar. 21, 2017.
CN Office Action for Chinese Application No. 201480015372.X dated Aug. 2, 2016.
CN Office Action for Chinese Application No. 20118004918.5 dated Jun. 15, 2015.
CN Office Action for Chinese Application No. 201180049184.5 dated Jul. 30, 2014.
CN Office Action for Chinese Application No. 201180049184.5 dated Mar. 4, 2016.
CN Office Action for Chinese Application No. 201380014845.X dated Dec. 23, 2016.
CN Office Action for Chinese Application No. 201380017644.5 dated Feb. 7, 2017.
CN Office Action for Chinese Application No. 201380017644.5 dated May 26, 2016.
CN Office Action for Chinese Application No. 201380017644.5 dated Sep. 29, 2015.
CN Office Action in Chinese Application No. 201380013988.9 mailed Oct. 27, 2015.
Daniel et al. "Implantable Diagnostic Device for Cancer Monitoring." Biosens Bioelectricon. 24(11): 3252-3257 (Jul. 15, 2009).
Database WPI, Week 201238, Thomson Scientific, London, GB; AN 2012-D49442.
De Lannoy et al., "Aquatic Biofouling Prevention by Electrically Charged Nanocomposite Polymer Thin Film Membranes", 2013 American Water Work Association membrane Technology Conference; Environmental science & technology 47.6 (2013): 2760-2768.
Deng et al., "Renal protection in chronic kidney disease: hypoxia-inducible factor activation vs. angiotensin II blockade," Am. J. Physiol. Renal Physiol. 299(6): F1365-F1373 (Dec. 2010) (available online Sep. 29, 2010).
Edwards, "Large Sheets of Graphene Film Produced for Transparent Electrodes (w/ Video)"; (Jun. 21, 2010), PhysOrg.com, retrieved on May 15, 2017 from https://phys.org/news/2010-06-large-sheets-graphene-transparentelectrodes.html (2 pages).
EP Office Action for European Application No. 13715529.7 dated Jun. 24, 2016.
Fayerman, "Canadian scientists use stem cells to reverse diabetes in mice", The Telegraph-Journal (New Brunswick), 1-2 (Jun. 29, 2012).
Fayerman, "Diabetes reversed in mice; University of B.C. scientists use embryonic stem cells to deal with Type 1 disease", The Vancouver Sun (British Columbia), 1-2 (Jun. 28, 2012).
Fejes et al. "A review of the properties and CVD synthesis of coiled carbon nanotubes." Materials 3.4 (2010): 2618-2642.
Franzen, C. "MIT Setting Up Industrial-Scale Graphene Printing Press" Sep. 23, 2011, retrieved from http://talkingpointsmemo.com/idealab/mit-setting-up-industrial-scale-graphene-printing-press (2 pages).
Freedman et al., "Genetic basis of nondiabetic end-stage renal disease," Semin. Nephrol. 30(2): 101-110 (Mar. 2010).
Garcia-Lopez et al., "Determination of high and low molecular weight molecules of icodextrin in plasma and dialysate, using gel filtration chromatography, in peritoneal dialysis patients," Peritoneal Dialysis Int'l 25(2): 181-191 (Mar. 2005-Apr. 2005).
Georgakilas et al., "Functionalization of Graphene: Covalent and Non-Covalent Approaches, Derivatives and Applications," Chem. Rev., (2012) 112(11), pp. 6156-6214.
Gnudi "Molecular mechanisms of proteinuria in diabetes," Biochem. Soc. Trans. 36(5): 946-949 (Oct. 2008).
Gotloib et al., "Peritoneal dialysis in refractory end-stage congestive heart failure: a challenge facing a no-win situation," Nephrol. Dialysis. Transplant. 20(Supp. 7): vii32-vii36 (Jul. 2005).
Han et al., "Ultrathin Graphene Nanofiltration Membrane for Water Purification." Advanced Functional Materials 23(29): 3693-3700 (Aug. 1, 2013).
Harvey "Carbon as conductor: a pragmatic view." Proceedings of the 61st IWCS Conference, http://www. iwcs. org/archives/56333-iwcs-2012b-1.1584632. vol. 1. 2012.
Hashimoto et al. "Direct evidence for atomic defects in graphene layers." Nature 430.7002 (2004): 870-873.
He, et al. "The attachment of Fe3 O4 nanoparticles to graphene oxide by covalent bonding." Carbon 48.11 (2010): 3139-3144.
Hone et al. "Graphene has record-breaking strength" Physicsworld.com, Jul. 17, 2008.
Huang et al., "Gene expression profile in circulating mononuclear cells afterexposure to ultrafine carbon particles," Inhalation Toxicol. 22(10): 835-846 (Aug 2010).
Humplik, et al. "Nanostructured materials for water desalination." Nanotechnology 22.29 (2011): 292001.
International Search Report and Written Opinion dated Jan. 5, 2012 for related International Application No. PCT/US11/47800.
International Search Report and Written Opinion dated Jul. 5, 2017 from related PCT application PCT/US2017/024147.
International Search Report and Written Opinion dated Mar. 12, 2014 for International Application No. PCT/US2013/074942.
International Search Report and Written Opinion for International Application No. PCT/US2011/047800 dated Jan. 5, 2012.

(56) References Cited

OTHER PUBLICATIONS

International Search Report and Written Opinion for PCT Application No. PCT/US2014/023027 dated Jun. 26, 2014.
International Search Report and Written Opinion in International Application No. PCT/US2013/030344 dated Jun. 19, 2013.
International Search Report and Written Opinion in International Application No. PCT/US2013/033035 dated Jun. 28, 2013.
International Search Report and Written Opinion in International Application No. PCT/US2013/033400, dated Jun. 28, 2013.
International Search Report and Written Opinion in International Application No. PCT/US2013/033403 dated Jun. 28, 2013.
International Search Report and Written Opinion in PCT/US2014/041766, dated Sep. 30, 2014.
International Search Report and Written Opinion dated Jun. 5, 2014 in International Application No. PCT/US2014/021677.
International Search Report and Written Opinion dated Jun. 6, 2014 in International Application No. PCT/US2014/023043.
International Search Report and Written Opinion dated Dec. 16, 2014, for International Application No. PCT/US2014/051011.
International Search Report and Written Opinion dated Jun. 19, 2015, in International Application No. PCT/US2015/020287.
Inui et al. "Molecular dynamics simulations of nanopore processing in a graphene sheet by using gas cluster ion beam." Applied Physics A: Materials Science & Processing 98.4 (2010): 787-794.
Israelachvili, "Intermolecular and Surface Forces," 3rd ed., Chap. 7.1, Sizes of Atoms, Molecules, and Ions, 2011, 1 page.
Jiao et al., "Castration differentially alters basal and leucine-stimulated tissue protein synthesis in skeletal muscle and adipose tissue," Am. J. Physiol. Endocrinol. Metab. 297(5): E1222-1232 (Nov. 2009) (available online Sep. 15, 2009).
JP Office Action in Japanese Application No. 2015-501729 dated Dec. 9, 2016 (English translation).
JP Office Action in Japanese Application No. 2015-501729 dated Jun. 20, 2017 (English translation).
JP Office Action in Japanese Application No. 2015-501867 dated Oct. 11, 2016 (English translation).
JP Office Action in Japanese Application No. 2015-503405 dated Nov. 14, 2016 (English translation).
JP Office Action in Japanese Application No. 2015-503406 dated Dec. 6, 2016(English translation).
Kang et al., "Effect of eplerenone, enalapril and their combination treatment on diabetic nephropathy in type II diabetic rats," Nephrol. Dialysis Transplant. 24(1): 73-84 (Jan. 2009).
Kang et al., "Efficient Transfer of Large-Area Graphene Films onto Rigid Substrates by Hot Pressing," American Chemical Society Nano, 6(6): 5360-5365(May 28, 2012).
Kar et al., "Effect of glycation of hemoglobin on its interaction with trifluoperazine," Protein J. 25(3): 202-211 (Apr. 2006) (available online Jun. 6, 2006).
Kawamoto et al., "Serum high molecular weight adiponectin is associated with mild renal dysfunction in Japanese adults," J. Atherosclerosis Thrombosis 17(11): 1141-1148 (Nov. 27, 2011).
Khun et al. "From Microporous Regular Frameworks to Mesoporous Materials with Ultrahigh Surface Area: Dynamic reorganization of Porous Polymer Networks" JACS, 2008; vol. 130; pp. 13333-13337.
Krupka et al., "Measurements of the Sheet Resistance and Conductivity of Thin Epitaxial Graphene and SiC Films" Applied Physics Letters 96, 082101-I; Feb. 23, 2010.
Kumar et al., "Modulation of alpha-crystallin chaperone activity in diabetic rat lens by curcumin," Molecular Vision 11: 561-568 (Jul 26, 2005).
Lathuiliere et al., "Encapsulated Cellular Implants for Recombinant Protein Delivery and Therapeutic Modulation of the Immune System," Journal of Applied Physics, Int. J. Mol. Sci., 16: 10578-10600 (May 8, 2015).
Lee, et al. "Measurement of the elastic properties and intrinsic strength of monolayer graphene." science 321.5887 (2008): 385-388.
Li, R.H. "Materials for immunoisolated cell transplantation". Adv. Drug Deliv. Rev. 33, 87-109 (1998).
Lucchese et al. "Quantifying ion-induced defects and Raman relaxation length in graphene." Carbon 48.5 (2010): 1592-1597.
Macleod et al. "Supramolecular Orderinng in Oligothiophene-Fullerene Monolayers" JACS, 2009, vol. 131, pp. 16844-16850.
Mattevi et al. "A review of chemical vapour deposition of graphene on copper." Journal of Materials Chemistry 21.10 (2011): 3324-3334.
Miao et al. "Chemical vapor deposition of grapheme" INTECH Open Access Publisher, 2011.
MIT/MTL Center for Graphene Devices and 2D Systems, retrieved from: http://www-mtl.mit.edu/wpmu/graphene/ [retrieved from Aug. 21, 2014 archive] (3 pages).
MIT/MTL Center for Graphene Devices and 2D Systems, retrieved from: http://www-mtl.mit.edu/wpmu/graphene/ [retrieved from Mar. 4, 2015 archive] (3 pages).
Nafea, et al. "Immunoisolating semi-permeable membranes for cell encapsulation: focus on hydrogels." J Control Release. 154(2): 110-122 (Sep. 5, 2011).
Nezlin, "Circulating non-immune IgG complexes in health and disease," Immunol. Lett. 122(2); 141-144 (Feb. 21, 2009) (available online Feb. 2, 2009).
Norata et al., "Plasma adiponectin levels in chronic kidney disease patients: relation with molecular inflammatory profile and metabolic status," Nutr. Metab. Cardiovasc. Dis. 20(1): 56-63 (Jan. 2010) (available online Apr. 9, 2009).
Ogawa et al., "Exosome-like vesicles in Gloydius blomhoffii blomhoffii venom," Toxicon 51(6): 984-993 (May 2008) (available online Feb. 19, 2008).
Ohgawara et al. "Assessment of pore size of semipermeable membrane for immunoisolation on xenoimplatntation of pancreatic B cells using a diffusion chamber." Transplant Proc. (6): 3319-3320. 1995.
Oki et al., "Combined acromegaly and subclinical Cushing disease related to high-molecular-weight adrenocorticotropic hormone," J. Neurosurg. 110(2): 369-73 (Feb. 2009).
Osorio et al., "Effect of treatment with losartan on salt sensitivity and SGLT2 expression in hypertensive diabetic rats," Diabetes Res. Clin. Pract. 86(3): e46-e49 (Dec. 2009) (available online Oct. 2, 2009).
Osorio et al., "Effect of phlorizin on SGLT2 expression in the kidney of diabetic rats," J. Nephrol. 23(5): 541-546 (Sep.-Oct. 2010).
Padidela et al., "Elevated basal and post-feed glucagon-like peptide 1 (GLP-1) concentrations in the neonatal period," Eur. J. Endocrinol. 160(1): 53-58 (Jan. 2009) (available online Oct. 24, 2008).
Pall Corporation, "Pall Water Processing Disc-Tube Filter Technology", Retrieved on Feb. 10, 2015, Retrieved from http://www.pall.com /pdfs/Fuels-and-Chemicals/Disc-Tube_Filter_Technology-DT100b.pdF (15 Pages).
Plant et al. "Size-dependent propagation of Au nanoclusters through few-layer grapheme," The Royal Society of Chemistry 2013, Nanoscale.
Pollard, "Growing Graphene via Chemical Vapor" Department of Physics, Pomona College; May 2, 2011.
Rafael et al. "Cell Transplantation and Immunoisolation: Studies on a macroencapsultaion device." From the Departments of Transplantation Pathology: Stockholm, Sweden (1999).
Rezania et al., "Enrichment of Human Embryonic Stem Cell-Derived NKX6.1—Expressing Pancreatic Progenitor Cells Accelerates the Maturation of Insulin-Secreting Cells In Vivo", Stem Cells Regenerative Medicine, vol. 31: 2432-2442 (Jul. 29, 2013).
Rezania et al., "Maturation of Human Embryonic Stem Cell-Derived Pancreatic Progenitors Into Functional Islets Capable of Treating Pre-existing Diabetes in Mice", Diabetes Journal, vol. 61: 2016-2029 (Aug. 1, 2012).
Ribeiro et al., "Binary Mutual Diffusion Coefficients of Aqueous Solutions of Sucrose, Lactose, Glucose, and Fructose in the Temperature Range from (298.15 to 328.15) K," J. Chem. Eng. Data 51(5): 1836-1840 (Sep. 2006) (available online Jul. 20, 2006).

(56) References Cited

OTHER PUBLICATIONS

Rippe et al., "Size and charge selectivity of the glomerular filter in early experimental diabetes in rats," Am. J. Physiol. Renal Physiol. 293(5): F1533-F1538 (Nov. 2007)(available online Aug. 15, 2007).
SA Final Rejection for Saudi Arabia Application No. 113340400 dated Jan. 28, 2016.
SA First Examination Report for Saudi Arabia Application No. 113340401 dated Apr. 28, 2015.
SA First Examination Report for Saudi Arabia Application No. 113340424 dated May 10, 2015.
SA First Examination Report for Saudi Arabia Application No. 113340426 dated May 12, 2015.
SA First Examination Report in Saudi Arabia Application No. 113340400 dated Apr. 13, 2015.
SA Second Examination Report for Saudi Arabia Application No. 113340400 dated Aug. 11, 2015.
Sanchez, et al. "Biological Interactions of Graphene-Family Nanomaterials—An Interdisciplinary Review." Chem Res Toxicol. 25(1): 15-34 (Jan. 13, 2012).
Sethna et al., "Serum adiponectin levels and ambulatory blood pressure monitoring in pediatric renal transplant recipients," Transplantation 88(8): 1030-1037 (Oct. 27, 2009).
Sullivan et al., "Microarray analysis reveals novel gene expression changes associated with erectile dysfunction in diabetic rats," Physiol. Genom. 23(2): 192-205 (Oct. 17, 2005) (available online Aug. 23, 2005).
Swett et al, "Imagining and Sculpting Graphene on the atomic scale" Oak Ridge National Laboratory's (ORNL) Center for Nanophase Materials Sciences (CNMS) Biannual Review. 1 page.
Swett et al, "Supersonic Nanoparticle Interaction with Suspended CVD Graphene", Microsc. Microanal. 22 (Suppl 3): 1670-1671 (Jul. 25, 2016).
Takata et al., "Hyperresistinemia is associated with coexistence of hypertension and type 2 diabetes," Hypertension 51. 2 (Feb. 2008): 534-9.
Tamborlane et al., "Continuous Glucose Monitoring and Intensive Treatment of Type 1 Diabetes" N Engl J Med 359;14: 1464-1476 (Oct. 2, 2008).
Tanugi et al., "Nanoporous Graphene Could Outperform Best Commercial Water Desalination Techniques," ; ACS 2012; Jun. 25, 2012; Weftec 2012; Sep. 29-Oct. 3.
Totani et al. "Gluten binds cytotoxic compounds generated in heated frying oil." Journal of oleo science 57.12 (2008): 683-690.
Tsukamoto et al. "Purification, characterization and biological activities of a garlic oliqosaccharide," Journal of UOEH 30. 2 (Jun. 1, 2008): 147-57.
TW Office Action in Taiwanese Application No. 102146079 dated Apr. 14, 2017.9 Pages.(English translation).
TW Search Report in Taiwanese Application No. 102146079 dated Apr. 14, 2017. 1 page.
Umea Universitet "Graphene nanoscrolls are formed by decoration of magnetic nanoparticles." ScienceDaily. Aug. 15, 2013. https://www.sciencedaily.com/releases/2013/08/130815084402.htm (3 pages).
U.S. Notice of Allowance for U.S. Appl. No. 12/868,150 dated Sep. 25, 2012.
U.S. Notice of Allowance for U.S. Appl. No. 13/548,539 dated Aug. 18, 2015.
U.S. Notice of Allowance for U.S. Appl. No. 13/548,539 dated Jul. 23, 2015.
U.S. Notice of Allowance for U.S. Appl. No. 13/719,579 dated May 20, 2016.
U.S. Notice of Allowance for U.S. Appl. No. 13/795,276 dated Oct. 7, 2016.
U.S. Notice of Allowance for U.S. Appl. No. 13/802,896 dated Apr. 1, 2015.
U.S. Notice of Allowance for U.S. Appl. No. 13/803,958 dated Aug. 29, 2016.
U.S. Notice of Allowance for U.S. Appl. No. 13/803,958 dated Jun. 2, 2016.
U.S. Notice of Allowance for U.S. Appl. No. 13/803,958 dated Sep. 12, 2016.
U.S. Notice of Allowance for U.S. Appl. No. 13/804,085 dated Jan. 15, 2015.
U.S. Notice of Allowance for U.S. Appl. No. 13/804,085 dated Mar. 12, 2015.
U.S. Notice of Allowance for U.S. Appl. No. 13/923,503 dated Oct. 14, 2016.
U.S. Notice of Allowance for U.S. Appl. No. 13/923,503 dated Oct. 5, 2016.
U.S. Notice of Allowance for U.S. Appl. No. 14/200,195 dated Jul. 5, 2016.
U.S. Notice of Allowance for U.S. Appl. No. 14/200,530 dated Aug. 1, 2016.
U.S. Notice of Allowance for U.S. Appl. No. 14/203,655 dated Dec. 9, 2016.
U.S. Notice of Allowance in U.S. Appl. No. 12/868,150 dated Sep. 25, 2012.
U.S. Notice of Allowance in U.S. Appl. No. 13/795,276 dated Jan. 19, 2017.
U.S. Notice of Allowance in U.S. Appl. No. 13/803,958 dated Aug. 29, 2016.
U.S. Notice of Allowance in U.S. Appl. No. 13/803,958 dated Sep. 12, 2016.
U.S. Notice of Allowance in U.S. Appl. No. 14/610,770 dated May 5, 2017.
U.S. Notice of Allowance in U.S. Appl. No. 14/656,580 dated May 8, 2017.
U.S. Notice of Allowance in U.S. Appl. No. 14/819,273 dated Jun. 9, 2017.
U.S. Notice of Allowance in U.S. Appl. No. 15/099,464 dated Jun. 16, 2017.
U.S. Office Action for U.S. Appl. No. 13/548,539 dated Feb. 6, 2015.
U.S. Office Action for U.S. Appl. No. 13/719,579 dated Jul. 8, 2015.
U.S. Office Action for U.S. Appl. No. 13/719,579 dated May 4, 2016.
U.S. Office Action for U.S. Appl. No. 13/795,276 dated Apr. 22, 2016.
U.S. Office Action for U.S. Appl. No. 13/795,276 dated Oct. 6, 2015.
U.S. Office Action for U.S. Appl. No. 13/802,896 dated Sep. 24, 2014.
U.S. Office Action for U.S. Appl. No. 13/803,958 dated Aug. 11, 2014.
U.S. Office Action for U.S. Appl. No. 13/803,958 dated May 28, 2015.
U.S. Office Action for U.S. Appl. No. 13/803,958 dated Nov. 18, 2015.
U.S. Office Action for U.S. Appl. No. 13/923,503 dated Mar. 22, 2016.
U.S. Office Action for U.S. Appl. No. 14/031,300 dated Jan. 20, 2016.
U.S. Office Action for U.S. Appl. No. 14/031,300 dated Jul. 7, 2015.
U.S. Office Action for U.S. Appl. No. 14/200,195 dated Mar. 21, 2016.
U.S. Office Action for U.S. Appl. No. 14/200,195 dated Nov. 4, 2015.
U.S. Office Action for U.S. Appl. No. 14/200,530 dated Feb. 29, 2016.
U.S. Office Action for U.S. Appl. No. 14/203,655 dated Aug. 10, 2016.
U.S. Office Action for U.S. Appl. No. 14/656,190 dated May 18, 2017.
U.S. Office Action for U.S. Appl. No. 14/656,657 dated Jul. 7, 2017.
U.S. Office Action for U.S. Appl. No. 14/686,452 dated Jun. 9, 2017.
U.S. Office Action for U.S. Appl. No. 14/843,944 dated Jun. 23, 2017.
U.S. Office Action for U.S. Appl. No. 14/856,471 dated May 31, 2017.
U.S. Office Action for U.S. Appl. No. 14/858,741 dated Dec. 1, 2016.

(56) References Cited

OTHER PUBLICATIONS

U.S. Office Action for U.S. Appl. No. 15/099,193 dated Jul. 19, 2017.
U.S. Office Action for U.S. Appl. No. 15/289,944 dated Feb. 9, 2017.
U.S. Office Action for U.S. Appl. No. 15/289,944 dated Jul. 13, 2017.
U.S. Office Action for U.S. Appl. No. 15/336,545 dated Dec. 19, 2016.
U.S. Office Action for U.S. Appl. No. 15/453,441 dated Jun. 5, 2017.
U.S. Office Action in U.S. Appl. No. 14/656,617 dated Apr. 4, 2017.
U.S. Office Action on U.S. Appl. No. 14/656,335 dated Apr. 25, 2017.
U.S. Office Action on U.S. Appl. No. 15/332,982 dated Jan. 30, 2017.
U.S. Supplemental Notice of Allowance for U.S. Appl. No. 13/795,276 dated Nov. 29, 2016.
Vallon, "Micropuncturing the nephron," Pflugers Archiv : European journal of physiology 458. 1 (May 2009): 189-201.
Van Der Zande et al. "Large-scale arrays of single-layer graphene resonators." Nano letters 10.12 (2010): 4869-4873.
Verdonck, P., "Plasma Etching", in Oficina de Microfabricao: Projeto e Construcao de CI's MOS, Swart, J.W., Ed., Campinas (Sao Paulo, Brazil): UNICAMP, 2006, ch. 10, p. 9.
Vlassiouk et al. "Large scale atmospheric pressure chemical vapor deposition of graphene." Carbon 54 (2013): 58-67.
Vriens et al. "Methodological considerations in quantification of oncological FDG PET studies." European journal of nuclear medicine and molecular imaging 37.7 (2010): 1408-1425.
Wang et al., "Direct Observation of a Long-Lived Single-Atom Catalyst Chiseling Atomic Structures in Graphene," Nano Lett., 2014, pp. A-F.
Wang et al., "Porous Nanocarbons: Molecular Filtration and Electronics," Advances in Graphene Science, Edited by Mahmood Aliofkhazraei, (2013) ISBN 978-953-51-1182-5, Publisher: InTech; Chapter 6, pp. 119-160.
Wang et al.,"What is the role of the second "structural" NADP+-binding site in human glucose 6-phosphate dehydrogenase?,"Protein science a publication of the Protein Society 17. 8 (Aug. 2008): 1403-11.
Wei et al., "Synthesis of N-doped graphene by chemical vapor deposition and its electrical properties", Nano Lett. 2009 9 1752-58.
Xiaogan Liang et al., Formation of Bandgap and Subbands in Graphene Nanomeshes with Sub-10nm Ribbon Width Fabricated via Nanoimprint Lithography., Nano Letters, Jun. 11, 2010, pp. 2454-2460.
Xie et al., "Fractionation and characterization of biologically-active polysaccharides from Artemisia tripartite," Phytochemistry 69. 6 (Apr. 2008): 1359-71.
Xie, et al. "Controlled fabrication of high-quality carbon nanoscrolls from monolayer graphene." Nano letters 9.7 (2009): 2565-2570.
Yagil et al. "Nonproteinuric diabetes-associated nephropathy in the Cohen rat model of type 2 diabetes" Diabetes 54. 5 (May 2005): 1487-96.
Zan et al. "Interaction of Metals with Suspended Graphene Observed by Transmission Electron Microscopy", J. Phys. Chem. Lett., Mar. 8, 2012, 3, 953-958.
Zhang et al. "Effect of Chemical Oxidation on the Structure of Single-Walled Carbon Nanotubes", J. Phys. Chem., Feb. 12, 2003, B 107 3712-8.
Zhang et al. "Method for anisotropic etching of graphite or graphene" Institute of Physics, Chinese Academy of Sciences; PEOP. Rep. China; Mar. 30, 2011.
Zhang et al. "Production of Graphene Sheets by Direct Dispersion with Aromatic Healing Agents", Small, May 6, 2010, vol. 6, No. 10, 1100-1107.
Zhang et al. "Isolation and activity of an alpha-amylase inhibitor from white kidney beans," Yao xue xue bao=Acta pharmaceutica Sinica 42. 12 (Dec. 2007): 1282-7.
Zhao, et al. "Efficient preparation of large-area graphene oxide sheets for transparent conductive films." ACS nano 4.9 (2010): 5245-5252.
Zhou, K., et al., "One-pot preparation of graphene/ Fe3O4 composites by a solvothermal reaction," New J. Chem., 2010, 34, 2950.
Zhu et al. "Carbon Nanotubes in Biomedicine and Biosensing", Carbon Nanotubes-Growth and Applications, InTech, (Aug. 9, 2011) Chapter 6: pp. 135-162. Available from: https://www.intechopen.com/books/carbon-nanotubes-growth-and-applications/carbon-nanotubes-in-biomedicine-and-biosensing.
Ziegelmeier et al. "Adipokines influencing metabolic and cardiovascular disease are differentially regulated in maintenance hemodialysis," Metabolism: clinical and experimental 57. 10 (Oct. 2008): 1414-21.
Zirk et al. "A refractometry-based glucose analysis of body fluids," Medical engineering & physics 29. 4 (May 2007): 449-58.
Zyga "Nanoporous Graphene Could Outperform Best Commercial Water Desalination Techniques," Phys.org., Jun. 22, 2012, Retrieved from http://www.phys.org/pdf259579929.pdf [Last Accessed Dec. 3, 2014] (3 pages).
U.S. Appl. No. 14/193,007, filed Feb. 28, 2014.
U.S. Appl. No. 14/856,471, filed Sep. 16, 2015.
U.S. Appl. No. 15/099,295, filed Apr. 14, 2016.
U.S. Appl. No. 15/099,410, filed Apr. 14, 2016.
U.S. Appl. No. 15/099,420, filed Apr. 14, 2016.
U.S. Appl. No. 15/099,289, filed Apr. 14, 2016.
U.S. Appl. No. 15/099,447, filed Apr. 14, 2016.
U.S. Appl. No. 15/099,269, filed Apr. 14, 2016.
U.S. Appl. No. 15/099,239, filed Apr. 14, 2016.
U.S. Appl. No. 15/099,464, filed Apr. 14, 2016.
U.S. Appl. No. 15/099,276, filed Apr. 14, 2016.
U.S. Appl. No. 15/099,482, filed Apr. 14, 2016.
U.S. Appl. No. 15/099,056, filed Apr. 14, 2016.
U.S. Appl. No. 15/099,099, filed Apr. 14, 2016.
U.S. Appl. No. 14/656,190, filed Mar. 12, 2015.
U.S. Appl. No. 15/099,304, filed Apr. 14, 2016.
U.S. Appl. No. 15/099,588, filed Apr. 14, 2016.
U.S. Appl. No. 14/707,808, filed May 8, 2015.
U.S. Appl. No. 14/819,273, filed Aug. 5, 2015.
U.S. Appl. No. 14/856,198, filed Sep. 16, 2015.
U.S. Appl. No. 14/754,531, filed Jun. 29, 2015.
U.S. Appl. No. 14/610,770, filed Jan. 30, 2015.
U.S. Appl. No. 14/656,657, filed Mar. 12, 2015.
U.S. Appl. No. 14/609,325, filed Jan. 29, 2015.
U.S. Appl. No. 14/656,580, filed Mar. 12, 2015.
U.S. Appl. No. 13/480,569, filed May 25, 2012.
U.S. Appl. No. 14/843,944, filed Sep. 2, 2015.
U.S. Appl. No. 15/099,193, filed Apr. 14, 2016.
U.S. Appl. No. 15/308,351, filed Nov. 1, 2016.
Notice of Allowance for U.S. Appl. No. 14/819,273 dated Oct. 28, 2016.
CN Office Action in Chinese Application No. 201580006829.5 dated Aug. 1, 2017. (English translation) (8 pages).
EP Office Action for European Application No. 15743307.9 dated Aug. 8, 2017. (17 pages).
European Search Report dated Aug. 28, 2017 from related EP application 15743750.0. (7 pages).
International Search Report and Written Opinion dated Aug. 14, 2017 from related PCT application PCT/US2017/031537. (12 pages).
Jiang, L. et al., Design of advanced porous grapheme materials: from grapheme nanomesh to 3D architectures. Nanoscale, Oct. 16, 2013, vol. 6, pp. 1922-1945.
JP Office Action in Japanese Application No. 2015-503405 dated Jun. 28, 2017. (English translation) (6 pages).
JP Office Action in Japanese Application No. 2015-549508 dated Jun. 27, 2017 (English translation) (7 pages).
Schweitzer, Handbook of Separation Techniques for Chemical Engineers, 1979, McGraw-Hill Book Company, pp. 2-5 to 2-8.

(56) References Cited

OTHER PUBLICATIONS

Search Report and Written Opinion dated Aug. 14, 2017 for Singapore Application No. 11201606287V. (10 pages).
Search Report and Written Opinion dated Aug. 22, 2017 for Singapore Application No. 11201607584P. (7 pages).
Sears et al., "Recent Developments in Carbon Nanotube Membranes for Water Purification and Gas Separation" Materials, vol. 3 (04 Jan. 2010), pp. 127-149.
U.S. Notice of Allowance in U.S. Appl. No. 14/610,770 dated Sep. 26, 2017. (12 pages).
U.S. Notice of Allowance in U.S. Appl. No. 14/656,580 dated Sep. 5, 2017. (8 pages).
U.S. Notice of Allowance in U.S. Appl. No. 15/332,982 dated Sep. 21, 2017. (5 pages).
U.S. Office Action for U.S. Appl. No. 14/609,325 dated Aug. 25, 2017. (7 pages).
U.S. Office Action for U.S. Appl. No. 15/332,982 dated Aug. 18, 2017. (9 pages).
EPO Extended Search Report for European Application No. 171684883.5 dated Jul. 25, 2017 (8 pages).
EPO Supplementary Search Report for European Application No. 15762019.6 dated Aug. 9, 2017 (16 pages).
U.S. Office Action in U.S. Appl. No. 15/099,099 dated Oct. 5, 2017 (11 pages).
U.S. Office Action in U.S. Appl. No. 15/099,447 dated Oct. 3, 2017 (21 pages).
Weisen, et al., "Fabrication of nanopores in a graphene sheet with heavy ions: a molecular dynamics study", Journal of Applied Physics 114, 234304 (2013), pp. 234304-1 to 234304-6.

\* cited by examiner

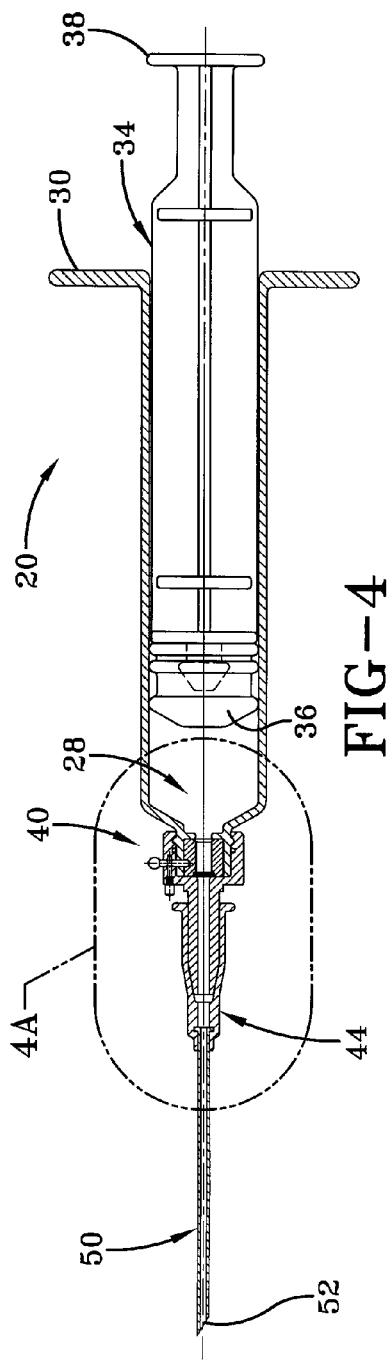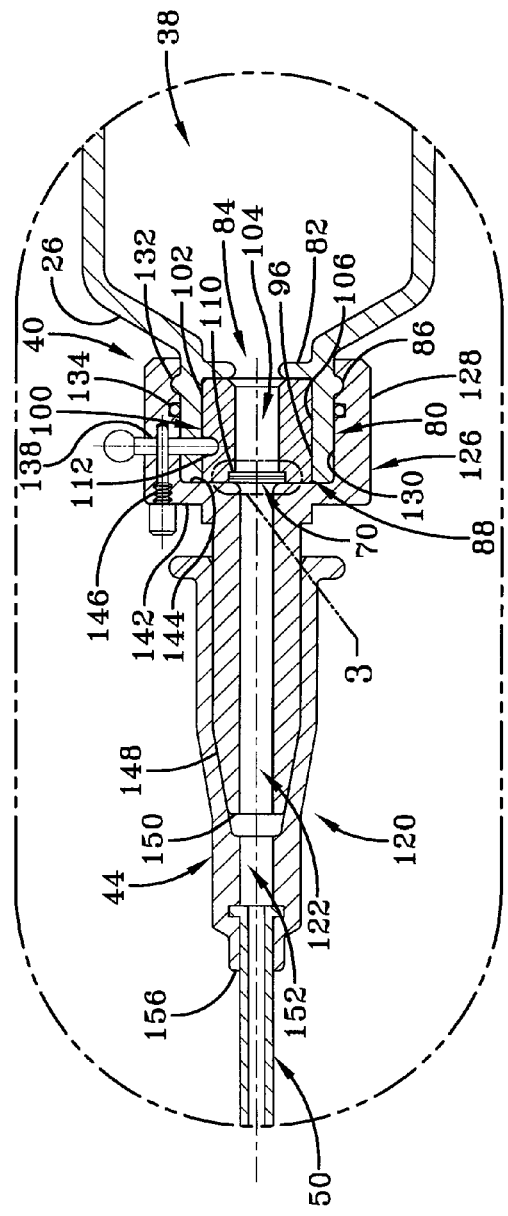
FIG-4
FIG-4A

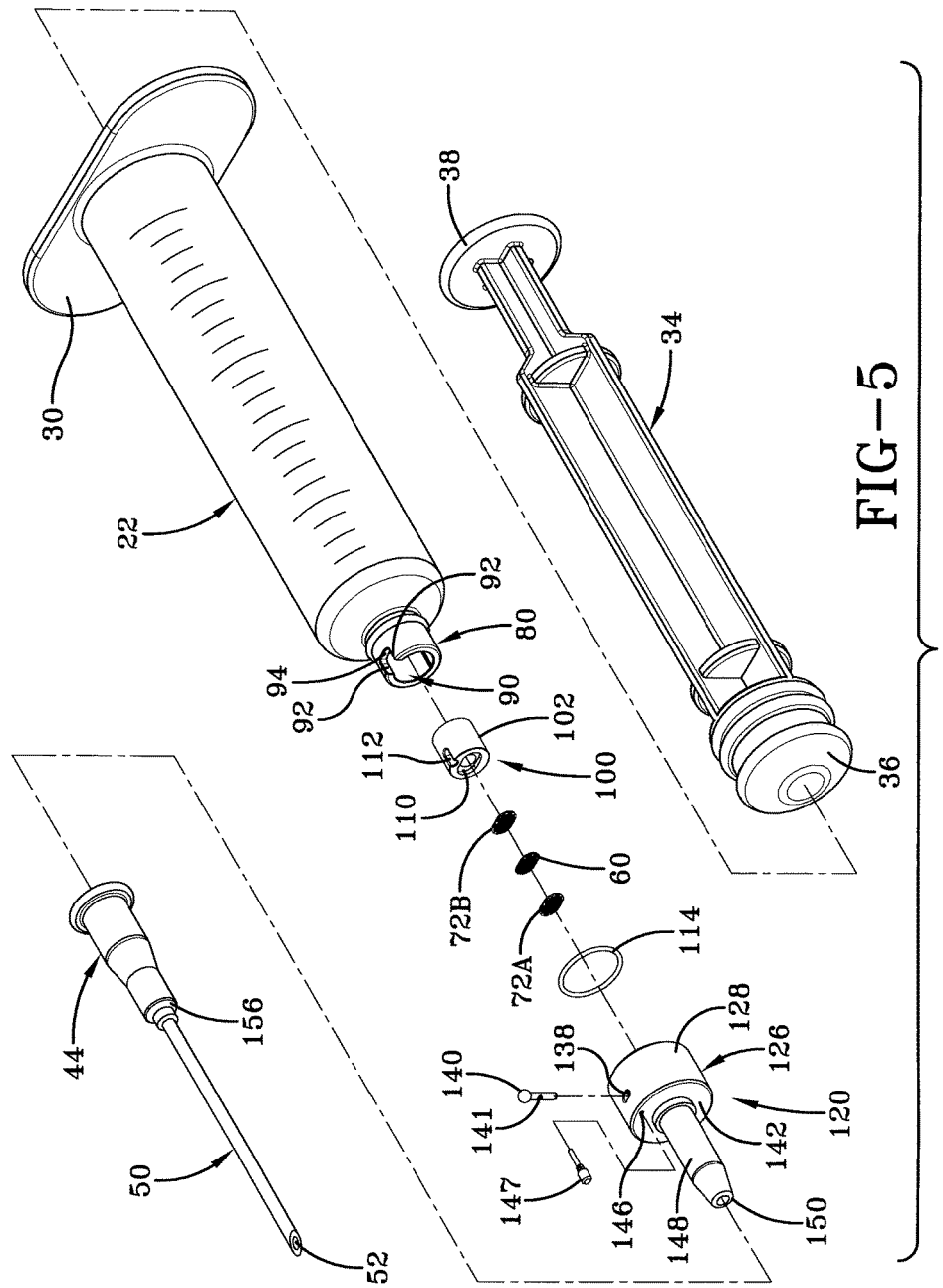

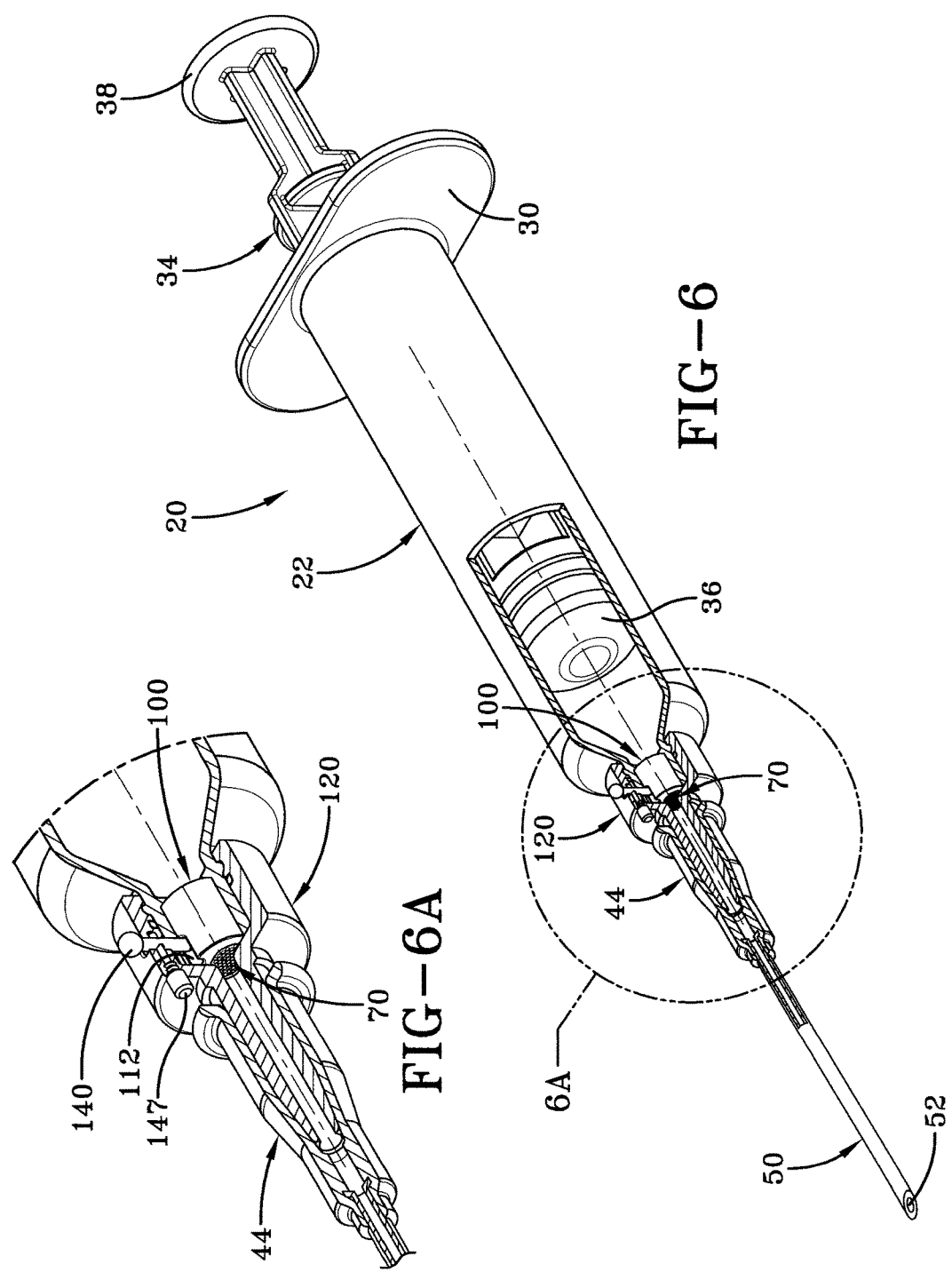

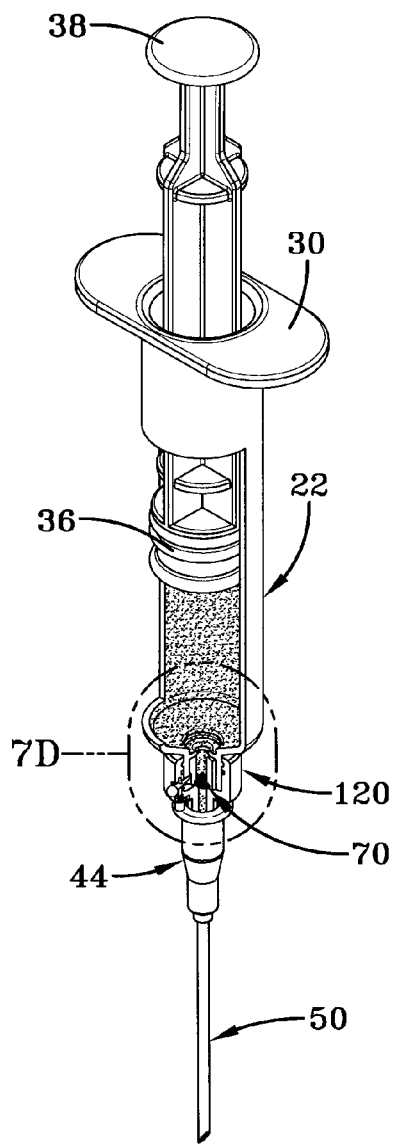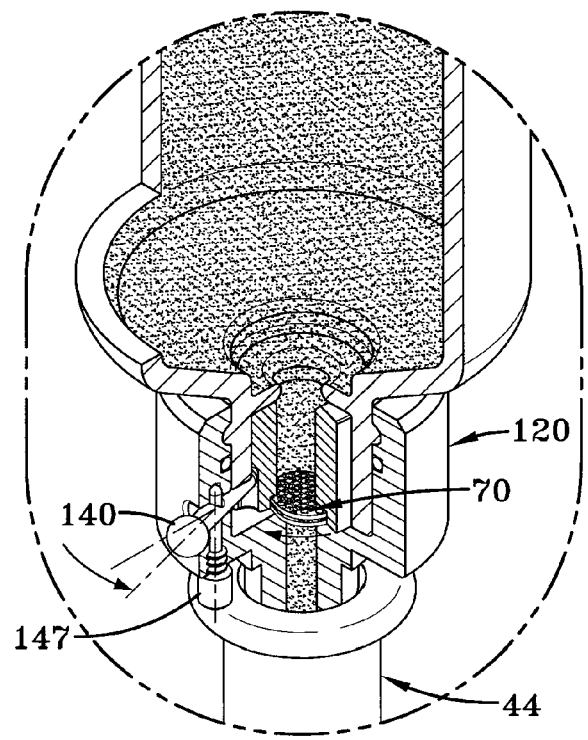
FIG-7C
FIG-7D

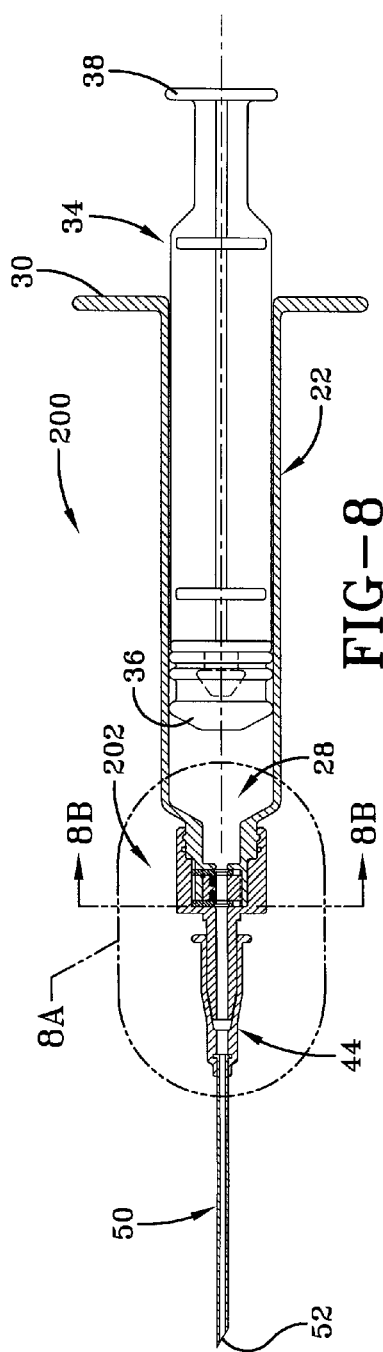
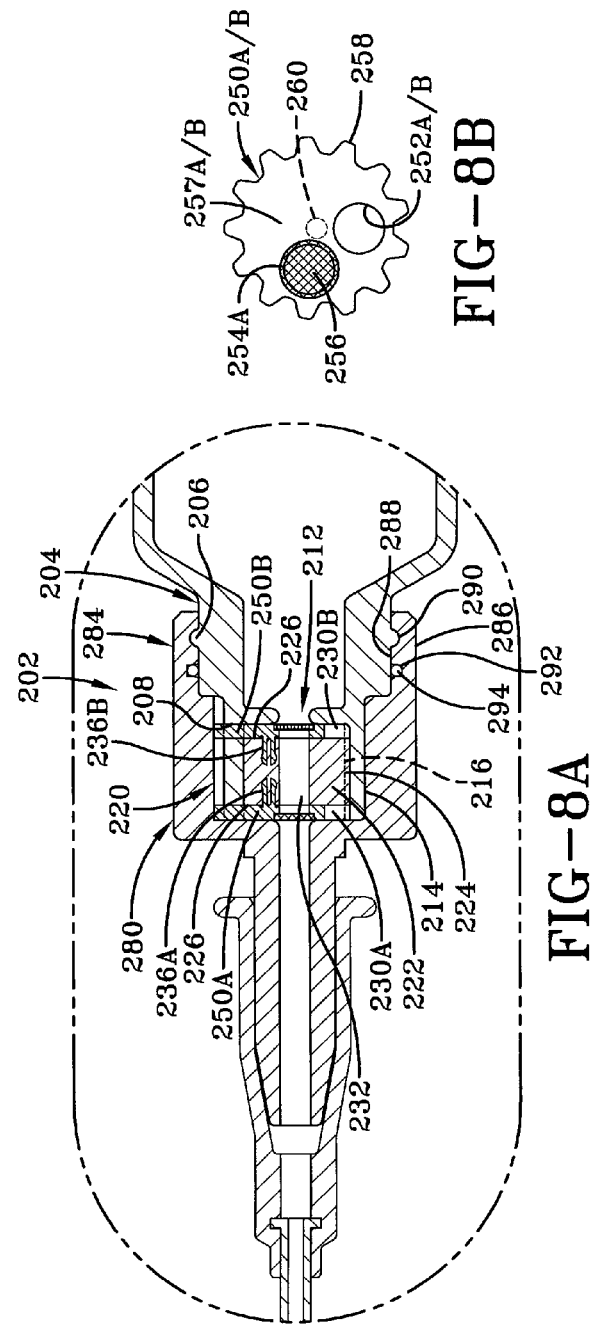

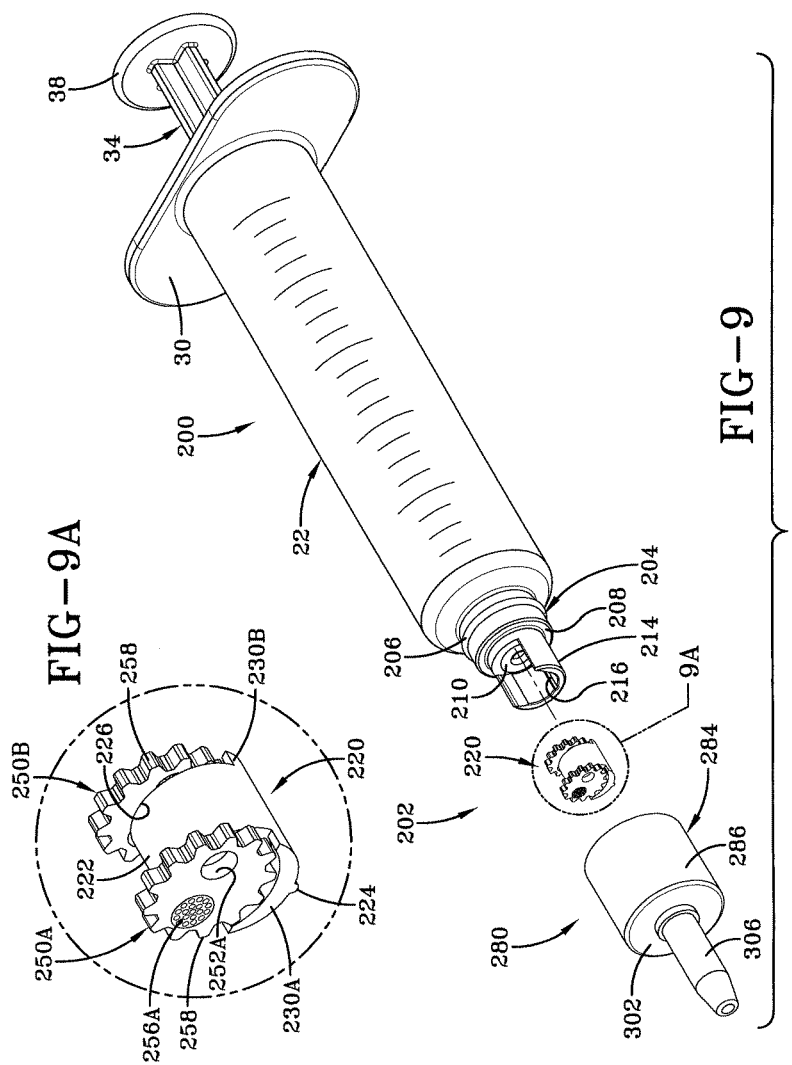

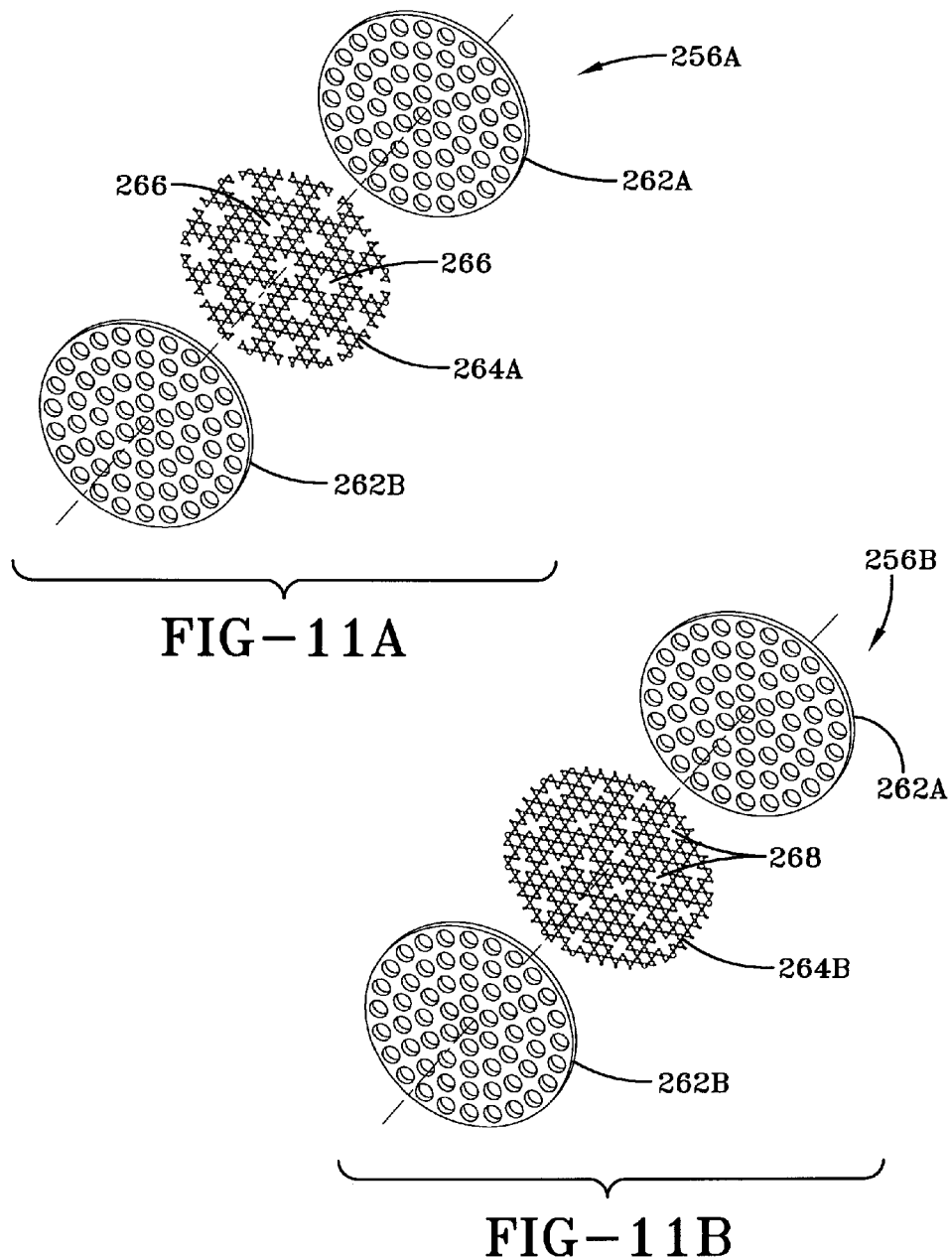

SYRINGE FOR OBTAINING NANO-SIZED MATERIALS FOR SELECTIVE ASSAYS AND RELATED METHODS OF USE

TECHNICAL FIELD

Generally, the present invention is directed to syringes. Specifically, the present invention is directed to syringes that capture nano-sized materials from a solution. More particularly, the invention is directed to a syringe with membranes having aperture sizes to selectively collect molecules within a predetermined range of sizes.

BACKGROUND ART

Current medical testing techniques are highly specific and require a number of individual devices and strategies to perform the testing. In medical testing, it is desirable to utilize tests and quantitative assay of specific agents such as virus, bacterium or toxin. Current testing procedures rely upon electro-chemical and pharmaceutical techniques which although effective, have certain shortcomings.

As well understood, an assay is an investigative/analytical procedure in laboratory medicine, pharmacology, environmental biology and molecular biology for qualitatively assessing or quantitatively measuring the presence or amount, or the functional activity of a target entity. The target entity is sometimes referred to as an analyte or the measurand or the target of the assay. In other words, the target entity is contained within a solution or other medium and which must be selectively accumulated so that the target entity can be further analyzed. One critical part of the assay process is collecting the sample for further analysis. Current systems do not allow for quick and defined collection of molecules of selected size range. For example, it may be desirable to analyze molecules ranging in size between 15 to 25 nanometers in diameter. Past methods might only collect molecules up to 25 nanometers and as a result molecules sized less than 15 nanometers in diameter will also be collected and these irrelevant smaller sized molecules may disrupt the testing of the sample. For example, it may be desirable to isolate a pathogen from blood plasma as a generalized test for the presence of a specific agent. Indeed, large molecules (e.g. heavy metal toxins), proteins (e.g. the prion responsible for mad cow disease) and distinct viruses including influenza and HIV occupy distinct bands within the size spectrum of 10 angstroms to 1000 angstroms.

Therefore, there is a need in the art for a syringe that can selectively obtain a range of specifically sized materials. Moreover, there is a need in the art to selectively obtain molecules which are sized in the nanometer range.

SUMMARY OF THE INVENTION

In light of the foregoing, it is a first aspect of the present invention to provide a syringe for obtaining nano-sized materials for selective assays and related methods of use.

It is another aspect of the present invention to provide a syringe for obtaining nano-sized components from a solution, comprising a barrel having a barrel interior, a needle extending from one end of the barrel, a plunger received in the barrel interior at an end of the barrel opposite the needle, and a filter cartridge maintained between the needle and the barrel, said filter cartridge maintaining at least one membrane having apertures of two distinct size ranges, wherein operation of the plunger to draw the solution into the barrel interior allows for retention of nano-sized components of a size between the two distinct size ranges.

Yet another aspect of the present invention is to provide a method of obtaining nano-sized components of a predetermined size range from a solution, comprising providing a syringe having a filter cartridge maintained between a needle and a barrel of the syringe, positioning at least one membrane maintained by the filter cartridge between the needle and the barrel, the at least one membrane having aperture sizes of two distinct ranges, and passing a solution through the at least one membrane having a first distinct aperture size range and through the at least one membrane having a second distinct aperture size range so as to retain nano-sized components of a size between the two distinct size ranges.

BRIEF DESCRIPTION OF THE DRAWINGS

These and other features and advantages of the present invention will become better understood with regard to the following description, appended claims, and accompanying drawings wherein:

FIG. 1 is a perspective view, partially cut away, showing a syringe made in accordance with the concepts of the present invention, and wherein FIG. 1A is a detailed view of the syringe with a general representation of a filter cartridge according to the concepts of the present invention;

FIG. 3 is a perspective view of a membrane assembly utilized in the filter cartridge according to the concepts of the present invention, wherein

FIG. 4 is a cross-sectional view of the syringe according to the concepts of the present invention, wherein FIG. 4A is a detailed view of the filter cartridge;

FIG. 5 is a perspective, exploded view of the syringe according to the concepts of the present invention;

FIG. 6 is a perspective view of the syringe, partially cut-away, showing a syringe made according to the concepts of the present invention, wherein FIG. 6A is a detailed view of the cut-away portion;

FIGS. 7A-F show various stages of operation of the syringe according to the concepts of the present invention;

FIG. 8 show a cross-sectional view of an alternative syringe made in accordance with the concepts of the present invention, wherein FIG. 8A is a detailed view of an alternative filter cartridge made in accordance with the concepts of the present invention, and where FIG. 8B is an elevational view of a gear incorporated into the alternative filter cartridge in accordance with the concepts of the present invention;

FIG. 9 is a perspective exploded view of the alternative syringe made in accordance with the concepts of the present invention, wherein FIG. 9A is a detailed view of a removable chamber that is part of the filter cartridge in accordance with the concepts of the present invention;

FIG. 11A is a membrane assembly utilized in the filter cartridge of the alternative syringe in accordance with the concepts of the present invention, and FIG. 11B is another membrane assembly also utilized in the filter cartridge of the alternative syringe in accordance with the concepts of the present invention.

DETAILED DESCRIPTION OF THE INVENTION

Generally, the present invention is directed to a hypodermic or other type of syringe equipped with a replaceable filter cartridge between a needle and barrel of the syringe. The cartridge may be interchangeable or removable and may include a membrane or membranes containing nano-filters providing different perforation sizes. Briefly, operation of the device is in the following steps. A membrane having perforation size A is positioned within the syringe and a specimen is extracted such as blood plasma, wherein the membrane rejects particles and dissolved molecules larger than perforation size A and retains material equal to or smaller than perforation size A. Another filter with a perforation size B, which is smaller than perforation size A, is positioned within the syringe. The syringe is then operated such that the remaining content of the syringe contains only molecular material with sizes between perforation size B and A. As a result, the selected molecular material can have a predetermined size range which can then be evaluated or processed further. The term "solution" as used herein may also be referred to as material or other similar terms. The "solution" contains components such as molecules, DNA, toxins, viruses or any other comparably sized material that is desired to be captured within the filter cartridge.

Figure 1:
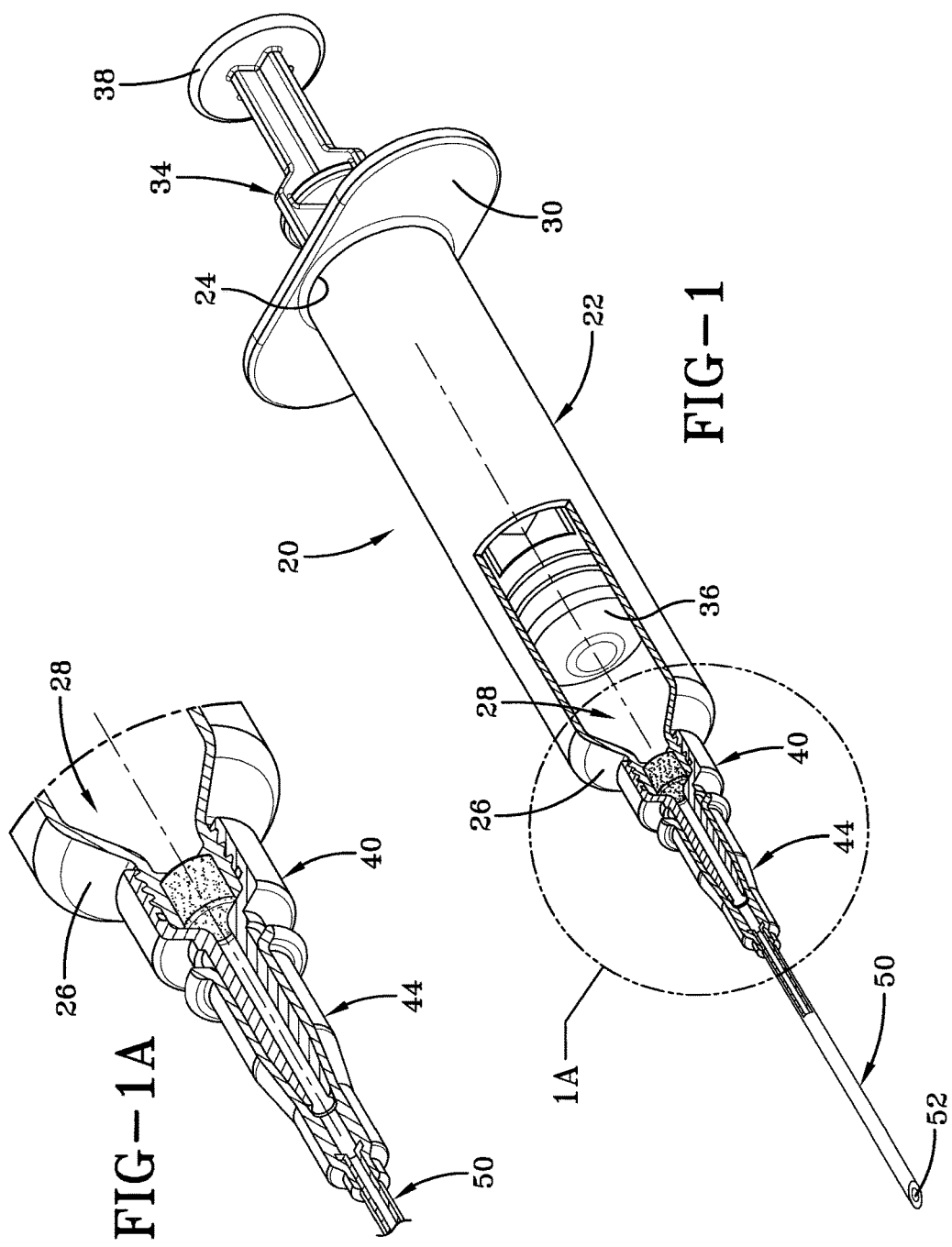

Referring now to FIG. 1, it can be seen that a syringe according to the concepts of the present invention is designated generally numeral 20. The syringe 20 provides a barrel 22 which is of a tubular construction. The barrel 22 has a plunger end 24 that is opposite a needle end 26. The barrel 22 provides an open interior 28. Extending radially from the plunger end 24 is a flange 30.

A plunger 34 is slidably received in the barrel 22. The plunger 34 includes a plunger tip 36 at one end which has an outer diameter sized to allow slidable movement within the interior 28. As skilled artisans will appreciate, the plunger tip 36 is sized to create enough of a seal to preclude migration of material from within the interior 28 while also generating a suction force at the needle end 26 when the plunger is pulled. Opposite the plunger tip 36 is a push end 38. Skilled artisans will appreciate the push end 38 may be manipulated by a user, or an automated mechanism or the like to move the plunger tip 36 in a desired direction. Suction mechanisms other than a plunger within a barrel may be utilized to pull or draw material through membranes with apertures as disclosed herein.

A filter cartridge 40 is maintained at the plunger end 24 of the barrel 22. As will be described in further detail, the filter cartridge 40 may be moveable and/or replaceable so as to allow for retention of desired size molecules or a size range of molecules in the interior 28 or an appropriate chamber. Details of this retention methodology and the related structural features of the filter cartridge will be discussed as the description proceeds.

A hub 44 is connected to an end of the filter cartridge 40 opposite the needle end 26 of the barrel. Extending from the hub 44 is a needle 50 which has a needle opening 52.

In general, the syringe 20 operates much like a standard syringe. Initially, the plunger tip 36 is moved to a position that is as close as possible to filter cartridge 40. The needle 50 is inserted into a solution which contains the solution with the molecular material and then the plunger or push end 38 is moved so as to generate a suction force that draws the solution in through the needle opening, through the filter cartridge 40 and into the barrel interior 28.

Figure 2:
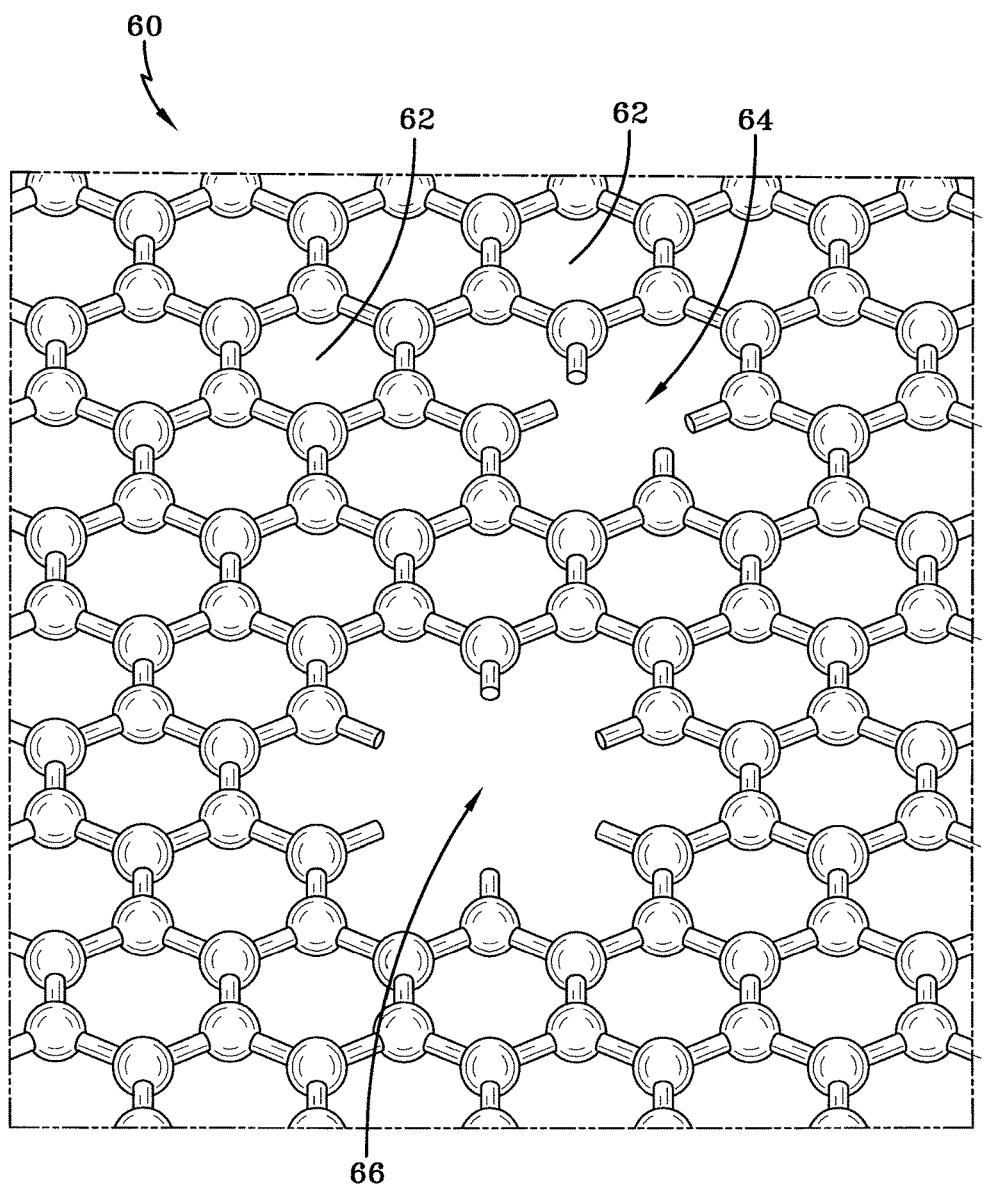
FIG. 2 is a schematic diagram of a graphene sheet utilized in the filter cartridge according to the concepts of the present invention.

Referring now to FIG. 2, it can be seen that a membrane is designated generally by the numeral 60. The membrane 60 is carried in the filter cartridge 40 and provides distinctive structural and operational features. Research and development efforts have resulted in the formation of materials such as graphene and, in particular, manufacturing processes that form relatively large scale quantities of consistent and uniform sheets and/or lengths of graphene material which may be employed as the membrane. The membrane 60 comprises a graphene sheet. In its most basic form the membrane comprises a sheet which may be in the form of a lattice or layer represented by interconnected hexagonal rings. In the disclosed embodiments, a graphene sheet may comprise a single layer of carbon atoms, or multiple layers of carbon atoms, which may be referred to as "few layer graphene." Skilled artisans will appreciate that single-layer or multi-layer graphene sheets may be formed, having greater thickness and correspondingly greater strength. Multiple graphene sheets can be provided in multiple layers as the sheet is grown or formed. Or multiple graphene sheets can be achieved by layering or positioning one sheet, which may be a single layer or few layer graphene, on top of another. For all the embodiments disclosed herein, a single sheet of graphene or multiple graphene sheets may be used and any number of layered sheets may be used. Testing reveals that multiple layers of graphene maintain their integrity and function as a result of self-adhesion. This improves the strength of the sheet. As seen in FIG. 2, the carbon atoms of the membrane 60 may define a repeating pattern of hexagonal ring structures (benzene rings) constructed of six carbon atoms, which form a honeycomb lattice of carbon atoms. An interstitial aperture 62 may be formed by each six-carbon atom ring structure in the sheet and this interstitial aperture is less than one nanometer across. Indeed, skilled artisans will appreciate that the interstitial aperture is believed to be about 0.23 nanometers (2.3 angstroms) across its longest dimension. Although an ideal configuration of the graphene sheet is shown in FIG. 2, skilled artisans will appreciate that imperfections in the bonding of carbon atoms to one another may result in corresponding imperfections in the sheet or sheets and, as a result, the interstitial aperture size may vary accordingly.

For the embodiments disclosed, the membrane 60 may be provided with two different aperture sizes. In particular, the membrane 60 may be provided with apertures 64 (only one is shown) which are relatively larger than the interstitial aperture. These apertures 64 may range from 5 angstroms to 1000 angstroms. The membrane 60 is also provided with apertures 66 (only one is shown) which are relatively larger than the apertures 64. In any of the embodiments to be discussed, the size of the apertures 66 may range anywhere from 5 angstroms to 1000 angstroms or more. As will be appreciated, the aperture sizes in the disclosed syringe embodiments do not overlap but are relative to one another. Moreover, the aperture sizes may be within a given range. By way of a non-limiting example, apertures 64 may be sized anywhere from 10 to 15 angstroms while apertures 66 may be sized anywhere from 45 to 50 angstroms. As a result, a range of molecules varying in size up to 40 angstroms may be obtained. Of course, smaller or larger ranges could be obtained. In most embodiments, the range of aperture sizes 64 are desirably kept to a minimum; however, wide ranges of aperture sizes 64 may be permissible in certain applications. In a similar manner, size ranges for apertures 66 may also be provided with different size ranges within a predetermined range. Skilled artisans will further appreciate that the carbon atoms that form the apertures 64 and 66 may be treated with certain functionalizations so as to repel particular properties of specimens contained within a solution or allow other particular specimens to pass through the membrane while repelling undesired materials. Various methodologies of generating apertures are being developed and may be utilized to obtain membranes utilized with the syringes disclosed herein.

Figure 3:
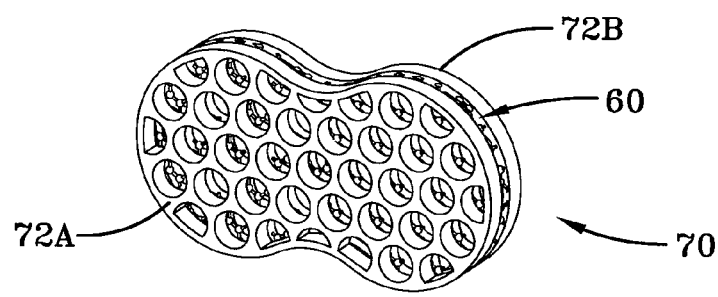
Figure 3A:
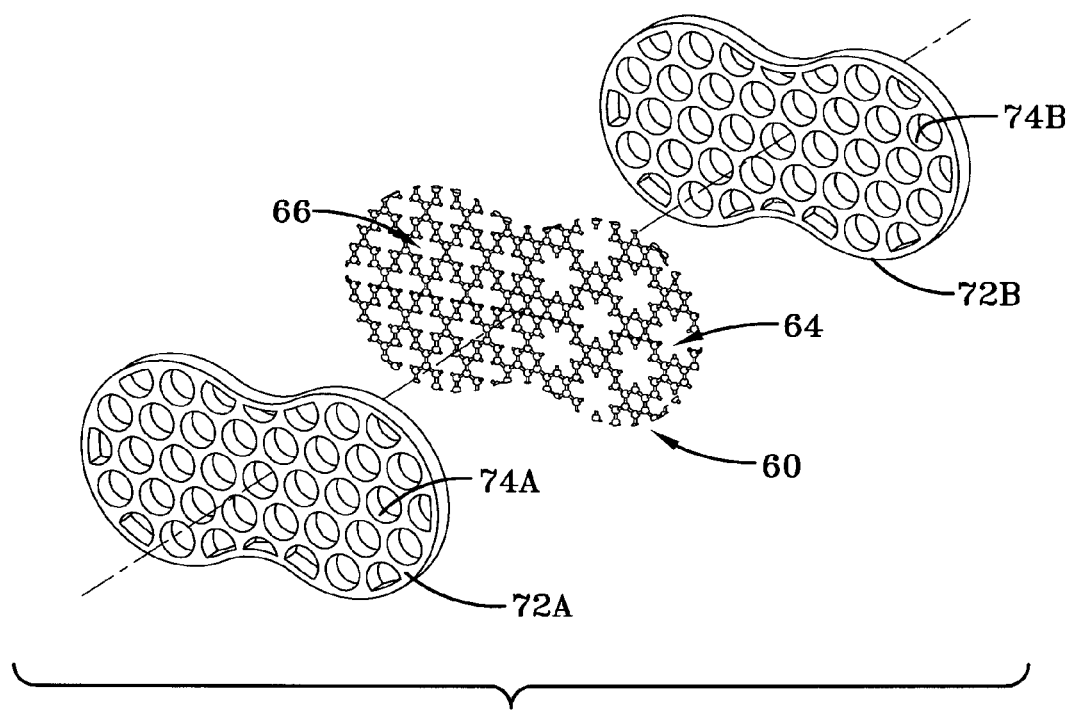
FIG. 3A shows an exploded perspective view of the membrane assembly.

Referring now to FIGS. 3 and 3A, it can be seen that a membrane assembly is designated generally by the numeral 70. The membrane assembly 70 is carried in the filter cartridge 40 and is structured such that the membrane 60 is captured between two mesh material screens 72A and 72B. Each screen 72A/72B provides for corresponding screen openings 74A/74B which are significantly larger than the apertures 64/66 provided by the membrane 60. In most embodiments, the screen 72 may be a non-woven material which is provided so as to provide structural support to the membrane 60. It will be appreciated that there is no particular alignment between the openings 74 and the apertures 64/66 of the membrane 60. In this particular embodiment, the only particular limitation is that the apertures 64 are disposed on one side or half of the membrane 60 while the other apertures 66 are disposed on the other side or half. As will become apparent as the description proceeds, the benefit of segregating the different sized apertures in two sides or halves will become apparent. The membrane assembly 70 may have an oval or other non-circular shape.

Referring now to FIGS. 4-6, details of the filter cartridge 40 will be provided. The filter cartridge 40 may be received in the needle end of the barrel interior 28 or in close proximity thereto. In particular, the needle end 26 provides a neck designated generally by the numeral 80. The neck 80 extends axially from the barrel interior 28 and provides an inwardly extending rim 82. The rim 82 has a rim opening 84 which is coaxial with the barrel interior and the needle opening 52. The neck 80 provides an annular nub 86 which extends radially outwardly therefrom. The neck 80 also provides a neck end 88. As best seen in FIG. 5, the neck end 88 provides a neck notch 90 wherein the notch 90 provides opposed sides 92 that are connected to the neck end 88 and a notch end 94 which connects the sides 92 to one another. The neck 80 is substantially tubular and the notch 90 provides for about a 15 to 35 degree opening. Skilled artisans will appreciate that other size openings may be provided and these openings may range anywhere from 10 to 90 degrees.

A membrane assembly holder designated generally by the numeral 100 is receivable in the neck 80. The membrane assembly holder 100 includes a holder body 102 sized to frictionally fit and be moveable within the rim opening 84. The holder body 102 has a body cavity 104 extending therethrough. The body cavity 104 is axially aligned with the rim opening 84 and the barrel interior 28. One end of the holder body 102 provides for an inset 110 which is of an oval or other non-circular shape. The inset 110 receives the membrane assembly 70 and in such a manner that the membrane assembly is substantially flush with an end of the holder body 102 and prevented from moving or rotating therein.

The holder body 102 also provides a holder channel 112 which extends from an end axially inward toward an opposite end of the body and on an exterior surface of the holder body 102. An O-ring 114 is sized to fit around the neck 80. The O-ring 114 will fit between the notch end 94 and the annular nub 86.

A cartridge cap is designated generally by the numeral 120 and snap-fits onto the neck 80. The cartridge cap 120 provides for a cap opening 122 extending axially therethrough wherein the opening 122 is substantially aligned with a needle opening 52 and the barrel interior 28. The cap 120 includes a cap collar 126. Skilled artisans will appreciate that the cartridge cap is made of a deflectable material and in particular the cap collar 126 is made of a deflectable material so as to allow for the cap collar to be deflected by the annular nub 86. As a result, the cartridge cap can be fit onto the neck simply by exerting an axial force so that the annular nub 86 is received in a nub groove. A similar deflection allows for removal of the cap collar.

The cap collar 126 provides for an exterior surface 128 opposite an interior surface 130. Maintained by the interior surface 130 is a nub groove 132 which is of an annular configuration and extends 360 degrees around the interior surface 130. In a similar manner, the interior surface 130 provides for a ring groove 134. The ring groove 134 receives the O-ring 114 while the nub groove 132 is sized to fit over the annular nub 86. Accordingly, when the cartridge cap 120 is pressed onto the neck 80, the membrane assembly holder 100 is captured therebetween.

The cap collar 126 includes a knob slot 138 extending radially through the cap collar. The knob slot 138 provides for reception of a knob shaft 140. The knob shaft 140 provides for a knob cross hole 141 extending radially therethrough. The cap collar 126 includes a cap base 142 which extends radially inwardly. The cap base 142 provides for an internal retention surface 144 which holds the membrane assembly 70 and membrane assembly holder 100 in place when the cap 120 is assembled to the neck 80. Extending through the cap base 142 is a pivot pin hole 146 which is aligned with the knob cross hole 141.

A pivot pin 147 is receivable in the pin hole 146 such that a distal end of the knob shaft 140 is received and maintained within the holder channel 112. The pivot pin 147 is received in the knob cross hole 141 and allows for the knob shaft 140 to pivot about the pivot pin 147. Pivoting of the knob shaft about pivot pin allows for controlled rotation or movement of the membrane assembly holder 100. In particular, the distal end of the knob is received in the holder channel 112 and deflection or pivoting of the pin 147 allows for slight rotation or re-positioning of the holder body 102 within the neck 80. As a result, the positioning of the distal end of the knob shaft to one side of the channel 112 provides for the half of the membrane 60 with the relatively larger openings 64 to be aligned with the needle opening 52 all the way through to the barrel interior. Movement of the knob shaft in an opposite direction to an opposite side of the channel 112 moves the membrane assembly such that the relatively smaller apertures are then aligned with the barrel interior and the needle opening.

The cap collar 126 includes a cap sleeve 148 which extends from the cap base 142 and is of a tapered construction. The cap sleeve has a sleeve opening 150 therethrough which is coaxial with the cap opening 122, the rim opening 84 and the barrel interior 28. The hub 44 has hub opening 152 therethrough and a needle end 156 which is secured to the needle 50.

Figure 7A:
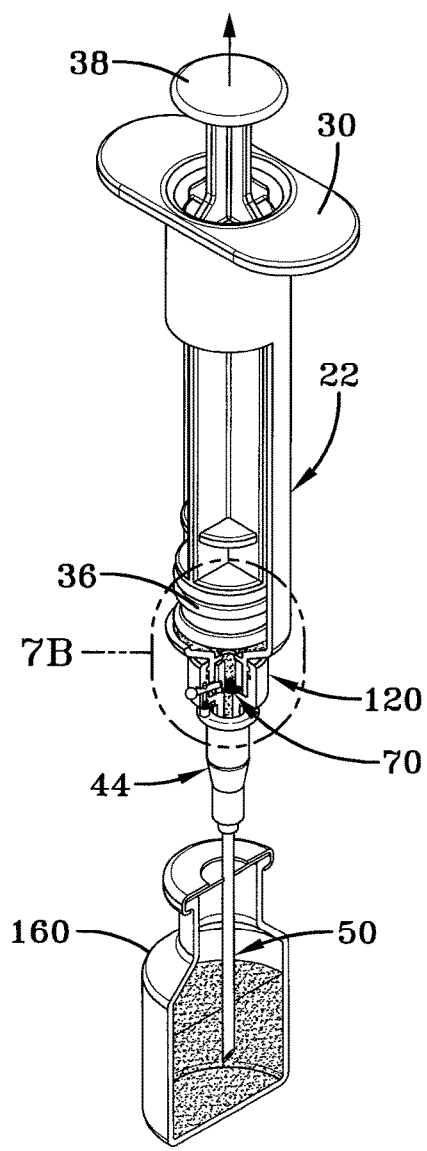
Figure 7B:
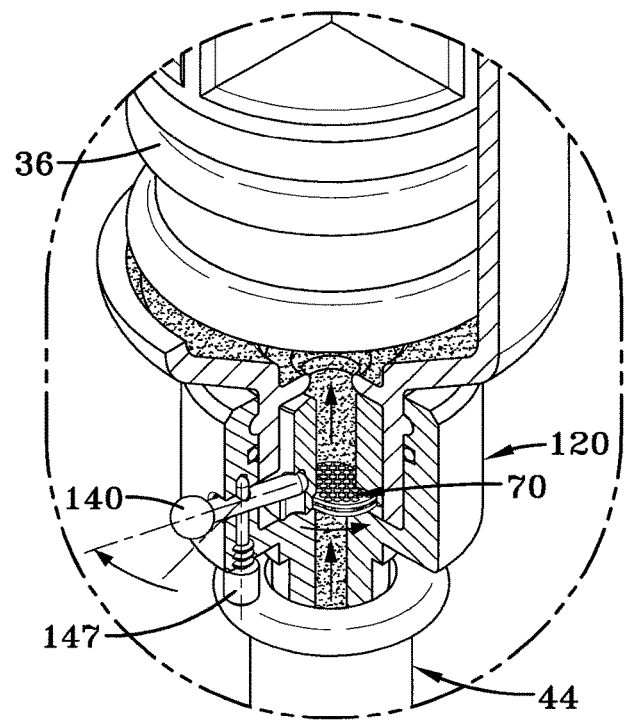

Referring now to FIGS. 7A-F operation of the syringe 20 will be described. Initially, the plunger is fully pressed into the interior barrel such that the plunger tip 36 is positioned as close as possible to the needle end 26. And in this position, the knob shaft 140 is moved, see FIG. 7B, such that the membrane assembly 70 and specifically the membrane 60 is positioned with the larger apertures 64, for example 25 to 30 angstroms, aligned with the openings throughout the syringe. In other words, the membrane 60 is aligned such that the material or solution with the desired components to be retained is pulled in by the plunger and directed through the apertures 64. As best seen in FIG. 7A, the needle 50 is inserted into a vial 160 or other container containing a solution which includes the material with the particular size that is desired to be further evaluated. At this time, a user or automated equipment pulls on the end 38 so as to generate a suction force that draws the material into the needle 50 and further through the filter cartridge 40. In particular, the material is pulled through the membrane 60 and the material sized less than the specified size range of apertures 64 is further pulled into the barrel interior 28 while the material sized larger than the apertures accumulates on the surface of the membrane assembly or within the needle and will not be allowed into the barrel interior.

Figures 7E, 7F:
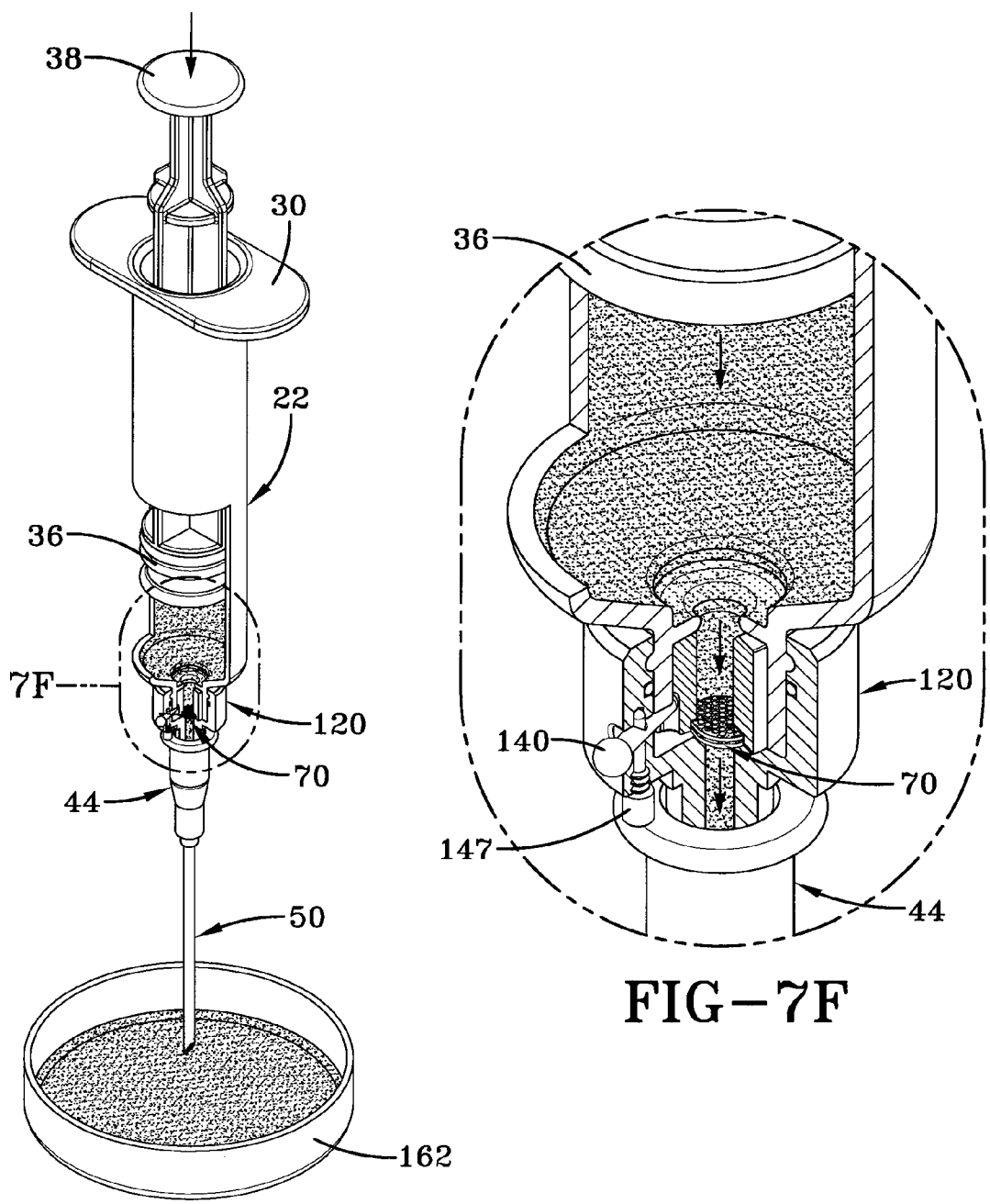

Turning now to FIGS. 7C and 7D, it can be seen that the knob shaft 140 is then pushed or pivoted to an opposite side of the notch 90 and accordingly moves the membrane assembly holder 100 such that the membrane 60 and in particular the portion of the membrane with apertures 66 which may be sized, by way of example only, 10 to 15 angstroms and are aligned with the various openings of the syringe. In particular, the apertures 66 are aligned with the needle opening, the barrel interior, the sleeve opening, the hub opening 152 and the rim opening 84. At this time the needle 50 is positioned over a collection dish 162 as seen in FIGS. 7E and 7F such that any material contained within the barrel that is smaller than the apertures 66 is pushed out of the syringe by directing the plunger back into the interior 28. As a result, the material left in the barrel is of the desired size range, for example between 15 to 30 angstroms. Upon completion of the plunger movement to push the material sized smaller than the apertures 66 out of the barrel, the material remaining in the barrel is the desired material of the appropriate size range. This desired size material can then be collected by completely withdrawing the plunger and pouring the material into an appropriate container or by removing the cap 126 and the holder and then pouring the material into an appropriate container. A suction device may also be used to withdraw the desired size range material.

Referring now to FIGS. 8, 8A, 8B, 9, and 9A, it can be seen that an alternative syringe is designated generally by the numeral 200. Unless otherwise indicated, the components within this syringe that are the same as the previous embodiment maintain the same identifying numbers. In this embodiment, the syringe 200 carries a filter cartridge 202 which, as in the previous embodiment, may be disposed between the barrel and the hub. Briefly, instead of the desired material being retained in the barrel of the syringe, the cartridge is maintained between the barrel and the hub and upon completion of the operation the desired material is removed from the cartridge.

In this embodiment, the barrel 22 extends to a neck designated generally by the numeral 204. The neck provides a radially outwardly extending annular nub 206 and the neck terminates at an end 208. Extending inwardly from the end 208 is a rim 210 which has a rim opening 210 extending therethrough. Extending from the neck end 208 is a cradle 214 best seen in FIG. 9.

In the embodiment shown, the cradle 214 extends more than 180 degrees. In other words, there is an opening of about 90 to 180 degrees between opposed edges of the cradle sides. The cradle 214 provides for an alignment slot 216.

Figure 10:
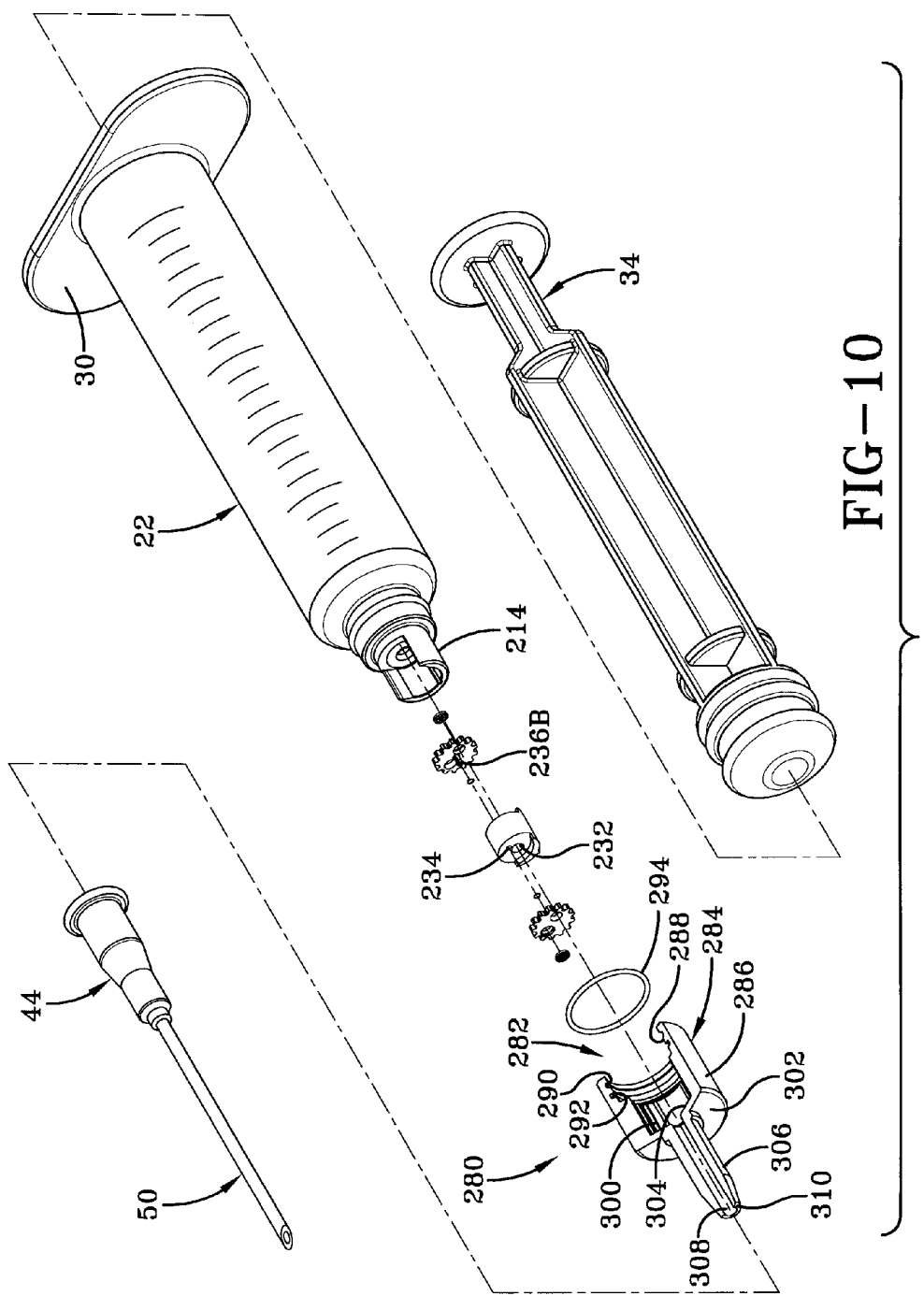
FIG. 10 is a perspective exploded view of the alternative syringe made in accordance with the concepts of the present invention.

The cartridge 202 includes a removable chamber 220 that is receivable in the cradle 214. The chamber 220 provides for a chamber housing 220 which has an alignment rib 224 at an underside thereof. This alignment rib 224 is receivable in the alignment slot 216 and prevents the chamber housing 222 from rotating side to side or otherwise laterally moving when received in the cradle 214. The chamber housing 222 provides for opposed chamber walls 226 at each end thereof. Extending from the chamber walls 226 in opposed directions are gear lips 230A and 230B. In particular, the lips extend from a bottom edge of the chamber wall and are curvilinear so as to match the outer diameter of the chamber housing 222. It will further be appreciated that the outer diameter and/or radius of the chamber housing is sized so as to be slidably received in the cradle 214. As best seen in FIG. 10, the chamber walls 226 each have a chamber opening 232 centrally disposed therethrough. These chamber openings 232 are aligned with the rim opening 212 and the interior of the barrel. Each chamber wall also provides for an axial opening 234. A gear washer 238 is provided around each axial opening 234. Received in each axial opening 234 is a gear 250. Gear 250A is proximal the needle while gear 250B is disposed proximal the barrel. As best seen in FIG. 8B, each gear 250 provides for a gear opening 252 which allows for unimpeded flow of fluid therethrough. The gear 250 also provides for a gear inset 254 which has an opening therethrough. The inset receives a corresponding membrane assembly 256. In other words, the membrane assembly 256A is received in inset 254A and membrane assembly 256B is received in inset 254B. Gear teeth 258 are disposed about the outer periphery of the gears 250 A/B. Extending axially from the center of the gear is a deflectable gear pin 260 which is receivable in the corresponding axial opening 234. In the present embodiment, the gear pin 260 has a deflectable head such that the gear is allowed to be snap-fit into the chamber housing and in particular the chamber wall 226. The fit of the gear pin is such that the gears 250 are permitted to rotate about their respective gear pins the syringe is fully assembled.

As seen in FIGS. 11A and 11B, each membrane assembly 256 includes a screen 262A and a screen 262B. A membrane 264A, which has the larger apertures 266 is disposed between screens 262A and 262B. In a similar manner, membrane assembly 256B includes a membrane 264B with relatively small apertures 268, wherein the membrane 264 is captured between corresponding screens 262A and 262B. As in the previous embodiment, the openings of the screens are significantly larger than the openings provided by the membranes 264A/B. As a result, the solution or material to be retained easily flows through the meshes but is filtered or stopped as appropriate depending upon the size of the apertures provided by the membranes. The apertures 266 and 268 may be sized in a manner similar to the apertures 64 and 66 as discussed previously.

A geared knob 280 is utilized to capture the chamber 220 between the needle 50 and the syringe barrel 22. The geared knob 280 has a knob opening extending axially therethrough. The geared knob 280 further provides for a knob collar 284 which includes an exterior surface 286 that is opposite an interior surface 288. The knob collar 284 is deflectable so that it fits onto and over the cradle 214. Provided within the interior surface 288 is a nub groove 290 and a ring groove 292. An O-ring 294 is received within the ring groove 292 while the nub groove 290 fits around the annular nub 206. Accordingly, the geared knob 280 fits onto the end of the barrel and in such a manner so as to capture the chamber 220 therebetween.

The knob collar 284, as best seen in FIG. 10, provides for a plurality of internal gear teeth 300 which mesh with the gear teeth 258 of both gears 250A/B. The knob collar provides for a knob base 302 which extends radially inward from the knob collar 284. An internal retention surface 304 captures the chamber 220 and in particular the lips 230 so as to hold the chamber 220 in place. Skilled artisans will appreciate that the geared knob is rotatable about the neck to permit rotation of the gears which allow for selective positioning and alignment of the opening 252, the membrane assembly 256, or a blocking portion of the gear in relation to the aligned openings of the syringe. Accordingly, by selectively positioning the geared knob or rotating the geared knob, a user is able to capture the desired material within the chamber housing 222. In other words, rotation of the knob collar 284 in one direction aligns the opening 252A and the membrane assembly 254B with all the coaxial openings of the syringe. Rotation of the knob collar in the opposite direction aligns the opening 252B and the membrane assembly 254A with all the coaxial openings of the syringe.

Extending from the geared knob 280 is a capsleeve 306 which has an opening 308 extending therethrough. The capsleeve 306 has a knob end 310 wherein the knob end is received with the hub 44. The hub 44 provides the hub opening 152 which is connected to the needle end 156.

Figure 12A:
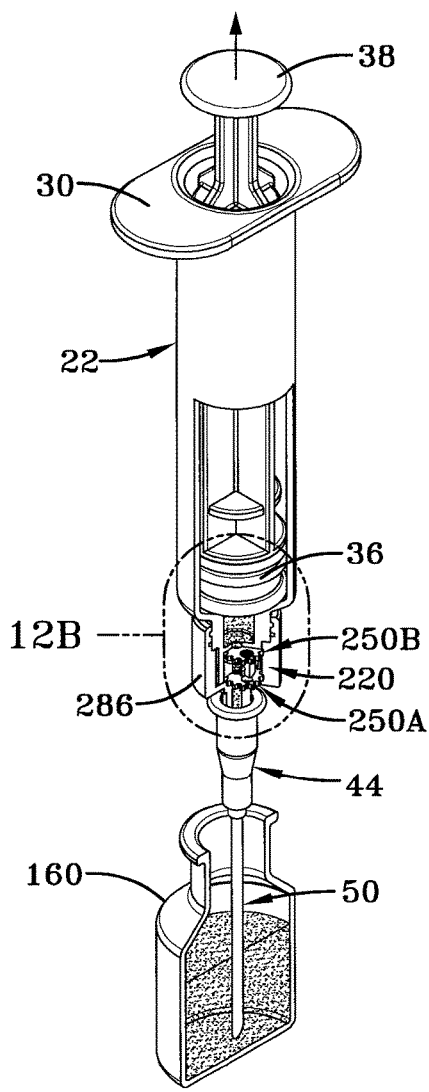
FIGS. 12A-F show various stages of operation for the alternative syringe in accordance with the concepts of the present invention.
Figure 12B:
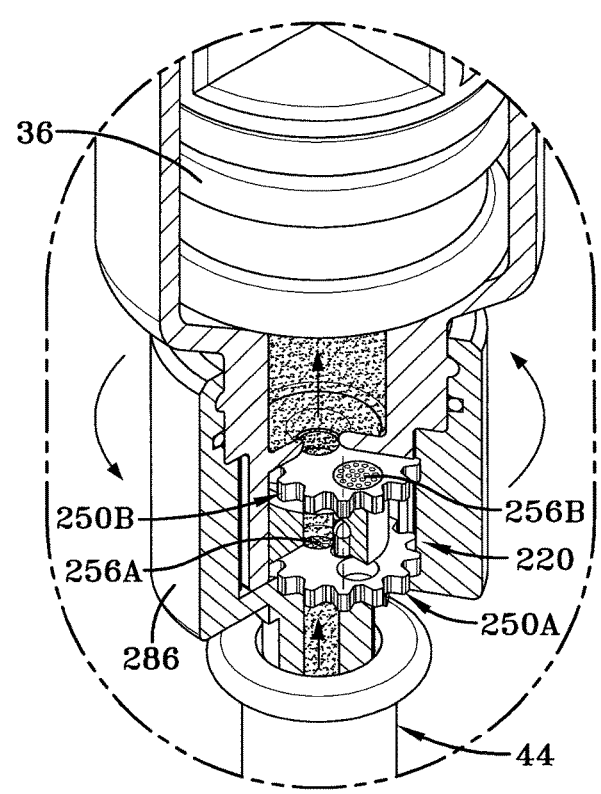

Referring now to FIGS. 12A-F, operation of the syringe 200 will be described. As best seen in FIGS. 12A and 12B, the geared knob is rotated such that the membrane assembly 256A and the opening 252B are aligned with the various openings of the syringe. In particular, the membrane assemblies are aligned with the barrel interior 28, the rim opening 212, the chamber openings 232, the knob opening 282, the capsleeve opening 308, the hub opening 152 and the needle opening 52. In this embodiment, the user will then pull on the plunger end 38 while the needle 50 is in a vial of the desired solution. As the end is pulled and suction force is created so as to draw the material within the vial into the chamber housing and into the barrel interior 28. As a result, the material that is sized smaller than the apertures 264A, provided by membrane assembly 256A, is received in the chamber housing 222.

Figure 12C:
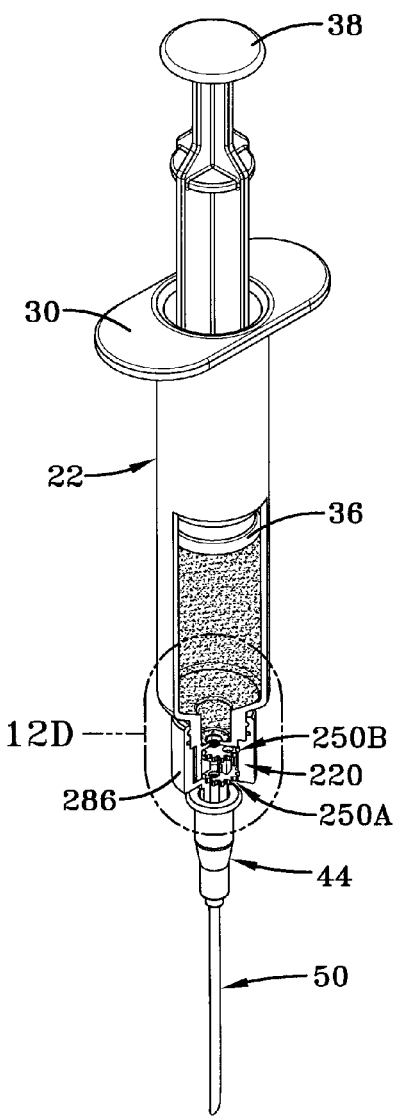
Figure 12D:
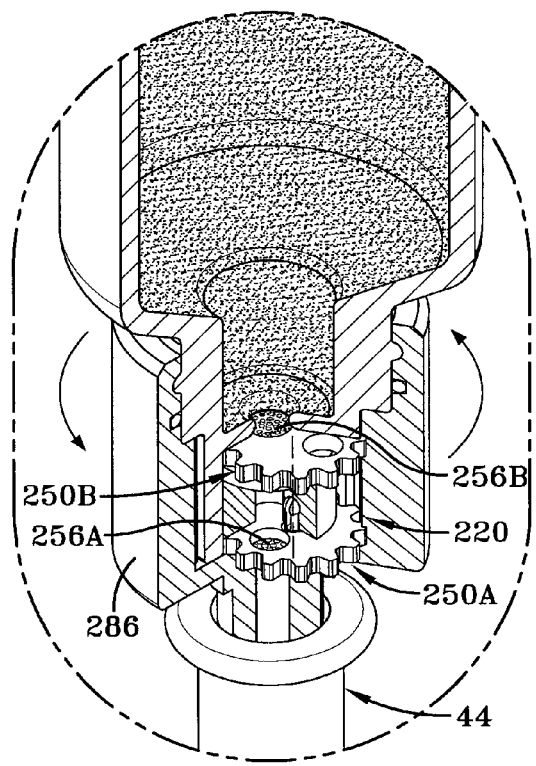
Figures 12E, 12F:
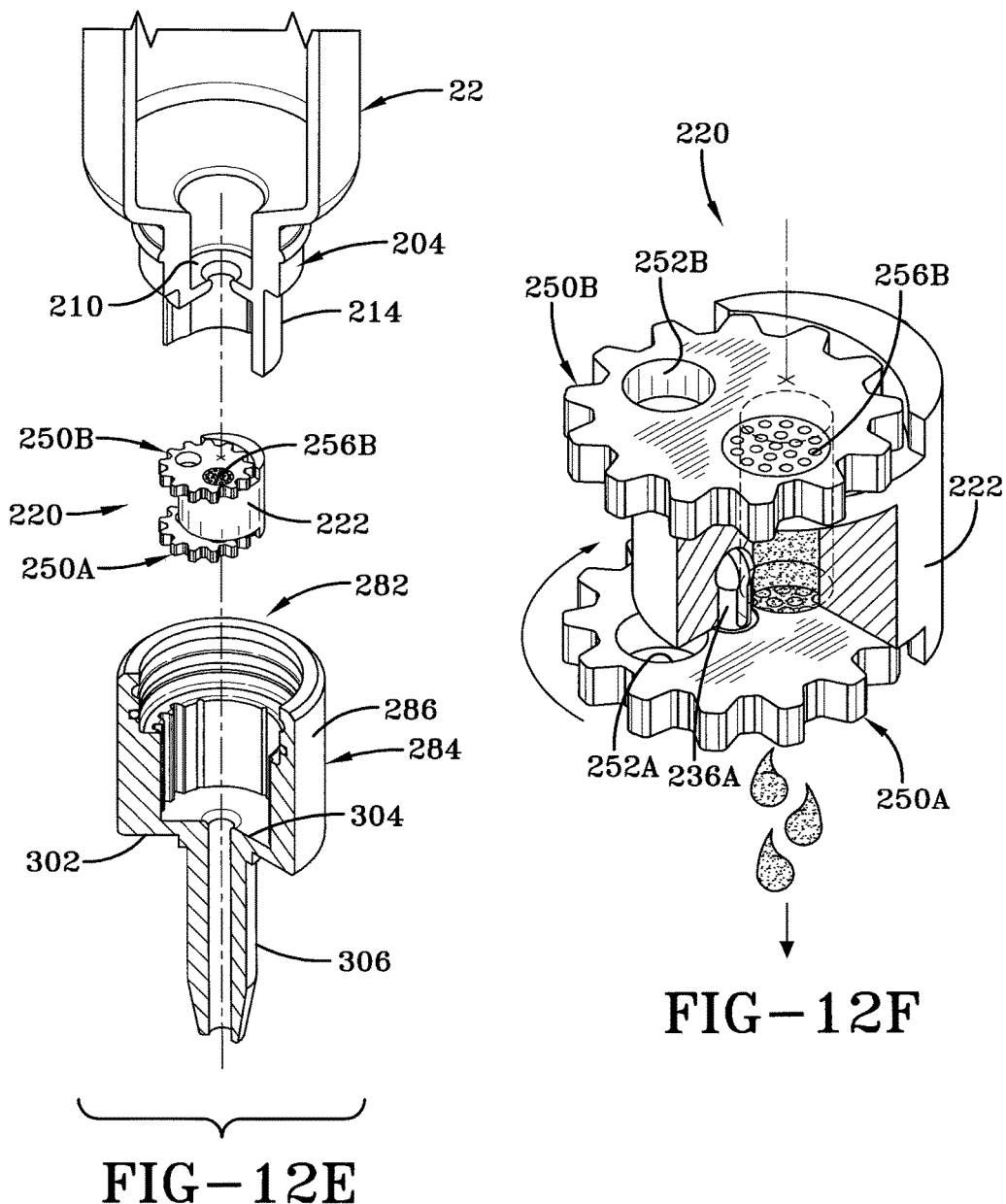

Referring now to FIGS. 12C and 12D it can be seen that the needle of the syringe is withdrawn from the selected material and that the geared knob may be rotated. As a result, the gear 250A closes one side of the chamber housing (the needle side) and the membrane assembly 256B is aligned with the barrel interior 28. The end of the plunger is then pulled further so as to draw the selected material that is smaller than the apertures 264B into the barrel interior 28 while retaining the desired size molecules which are larger than the apertures 264B within the chamber. The geared knob can then be rotated further so as to move both the gears 250A and 250B to a closed position as shown in FIG. 12E. At this time, as shown in FIG. 12F, the geared knob can be disassembled from the syringe and the chamber housing can be withdrawn from the cradle. The material that is retained within the chamber housing may then be transferred for evaluation.

The advantages of the present invention are readily apparent. Either embodiment allows for the capture of a range of different size molecules. For example, if one membrane has apertures sized for about 50 nanometers and the other membrane has a size to retain molecules about 25 nanometers, operation of the syringe as disclosed herein would allow for retention of molecules sized between 25 and 50 nanometers. Skilled artisans will appreciate that any size range could be employed by selectively choosing the membrane aperture sizes. As a result, a simple use of the disclosed syringe allows for performance of a wide range of biomedical assay functions. Such a configuration can replace a wide variety of conventional test procedures currently in use. Indeed, such a system and method for retention allows or testing for the presence of bio-agents including viruses, bacteria and toxins and for performing quantitative assay of blood, urine, spinal fluid and the like.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A syringe for obtaining nano-sized components from a solution, comprising:
   a barrel having a barrel interior;
   a needle extending from one end of the barrel;
   a plunger received in the barrel interior at an end of the barrel opposite the needle;
   a filter cartridge maintained between the needle and the barrel, the filter cartridge having at least one membrane having apertures of a first distinct size range and apertures of a second distinct size range, and
   wherein the apertures of the first distinct size range are positioned on one half of the at least one membrane and the apertures of the second distinct size range are positioned on an opposite half of the at least one membrane, and
   wherein the apertures of the first distinct size range are larger than the apertures of the second distinct size range.

2. The syringe according to claim 1, wherein the at least one membrane is graphene and the apertures of the first distinct aperture size range are 10 to 1000 angstroms in diameter and the apertures of the second distinct aperture size range are 10 to 1000 angstroms in diameter.

3. The syringe according to claim 2, wherein the apertures of the first distinct size range and the apertures of the second distinct size range are sized to capture nano-sized components in a range up to 40 angstroms.

4. The syringe according to claim 1, wherein:
   The syringe further comprises a hub connected to an end of the filter cartridge opposite a needle end of the barrel.

5. The syringe according to claim 4, wherein the at least one membrane is in the second position when the solution previously drawn into the barrel interior is pushed out of the barrel interior through the flow path by the plunger, the barrel retaining components that are sized between the first distinct size range and the second distinct size range.

6. The syringe according to claim 1, wherein the filter cartridge further comprises a knob shaft configured to move the at least one membrane between the first position and the second position.

7. A syringe for obtaining nano-sized components from a solution, comprising:
   a barrel having a barrel interior;
   a needle extending from one end of the barrel;
   a plunger received in the barrel interior at an end of the barrel opposite the needle;

a filter cartridge maintained between the needle and the barrel, the filter cartridge comprising:
  a chamber movable between a first position and a second position;
  a first membrane having apertures of a first distinct size range, the first membrane being disposed on one side of the chamber; and
  a second membrane having apertures of a second distinct size range, the second membrane being disposed on an opposite side of said chamber; and
a flow path across the chamber from the needle to the barrel interior,
wherein, in the first position, the first membrane is in the flow path, and
wherein, in the second position, the second membrane is in the flow path.

8. The syringe according to claim 7, wherein the first membrane is positioned closest to the needle and the first distinct size range is larger than the second distinct size range.

9. The syringe according to claim 8, wherein the chamber retains components sized between the first distinct size range and the second distinct size range.

10. The syringe according to claim 7, wherein the filter cartridge further comprises a geared knob configured to move the chamber between the first position and the second position.

* * * * *